US012736531B2

(12) United States Patent
Chanda et al.

(10) Patent No.: US 12,736,531 B2
(45) Date of Patent: Sep. 15, 2026

(54) METHOD FOR DETECTING VIRUS USING SSDNA FUNCTIONALIZED SENSOR

(71) Applicant: UNIVERSITY OF CENTRAL FLORIDA RESEARCH FOUNDATION, INC., Orlando, FL (US)

(72) Inventors: Debashis Chanda, Oviedo, FL (US); Abraham Vazquez-Guardado, Evanston, IL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 1084 days.

(21) Appl. No.: 17/661,141

(22) Filed: Apr. 28, 2022

(65) Prior Publication Data

US 2022/0411885 A1 Dec. 29, 2022

Related U.S. Application Data

(60) Provisional application No. 63/202,894, filed on Jun. 29, 2021.

(51) Int. Cl.
*G01N 33/543* (2006.01)
*B01L 3/00* (2006.01)
*C12N 15/115* (2010.01)

(52) U.S. Cl.
CPC .................. *G01N 33/54373* (2013.01); *B01L 3/502715* (2013.01); *B01L 3/502753* (2013.01); *B01L 3/502761* (2013.01); *B01L 2300/0877* (2013.01); *C12N 15/115* (2013.01); *G01N 2333/185* (2013.01)

(58) Field of Classification Search
CPC ......... G01N 33/54373; G01N 2600/00; G01N 21/554; C12N 15/115; B01L 2300/0819
See application file for complete search history.

(56) References Cited

FOREIGN PATENT DOCUMENTS

GB 2570909 A * 8/2019 ........... G01N 21/554

OTHER PUBLICATIONS

Vazquez-Guardado et al. "Enzyme-Free Plasmonic Biosensor for Direct Detection of Neurotransmitter Dopamine from Whole Blood" Nano Lett. 2019, 19, 449-454. (Year: 2019).*

Gou et al. "Nanoarray-Based Biomolecular Detection Using Individual Au nanoparticles with Minimized Localized Surface Plasmon Resonance Variations", Analytical Chemistry, 2011, 83, 2605-2612. dx.doi.org/10.1021/ac200432c (Year: 2011).*

Chowdhury, A. D.; Takemura, K.; Khorish, I. M.; Nasrin, F.; Ngwe Tun, M. M.; Morita, K.; Park, E. Y. The Detection and Identification of Dengue Virus Serotypes with Quantum Dot and AuNP Regulated Localized Surface Plasmon Resonance. Nanoscale Adv. 2020, 2 (2), 699-709. (Year: 2020).*

Cetin et al., "Plasmonic Nanohole Arrays on a Robust Hybrid Substrate for Highly Sensitive Label-Free Biosensing" ACS Photonics 2015 2 (8), 1167-1174 DOI: 10.1021/acsphotonics.5b00242 (Year: 2015).*

Dolot et al. "Crystal structures of thrombin in complex with chemically modified thrombin DNA aptamers reveal the origins of enhanced affinity", Nucleic Acids Research, 2018, 46:9, 4819-4830. doi: 10.1093/nar/gky268 (Year: 2018).*

Vit et al. "Perfusion microbioreactor system with permeable membranes to monitor bacterial growth", J. Chem Technol Biotechnol, 2019, 94: 712-720. DOI 10.1002/jctb.5814 (Year: 2019).*

Shuman et al., "The measurement of thrombin in clotting blood by radioimmunoassay", J Clin Invest. 1976;58(5):1249-1258. https://doi.org/10.1172/JCI108579. (Year: 1976).*

Yu, L., Li, C. M., Zhou, Q., & Luong, J. H. (2007). Poly(vinyl alcohol) functionalized poly(dimethylsiloxane) solid surface for immunoassay. Bioconjugate Chemistry, 18(2), 281-284. https://doi.org/10.1021/bc060108p (Year: 2007).*

Vazquez-Guardado et al. "Enzyme-Free Plasmonic Biosensor for Direct Detection of Neurotransmitter Dopamine from Whole Blood" Nano Lett. 2019, 19, 449-454.

Guner et al. "A smartphone based surface plasmon resonance imaging (SPRi) platform for on-site biodetection" Sensors and Actuators B 239 (2017) 571-577.

Liu et al. "Surface Plasmon Resonance Biosensor Based on Smart Phone Platforms" Scientific Reports | 5:12864 | DOI: 10.1038/srep12864; pp. 9.

LSU "LSU BS Fellow, ME Professor Create Sensor to Detect COVID-19" https://www.lsu.edu/eng/news/2021/01/covidsensor.php#:~: text=The smartphone-based device uses,strikes the nanostructure metal surface; Jan. 21, 2021 pp. 3.

Vazquez-Guardado et al. "Hybrid cavity-coupled plasmonic biosensors for low concentration, , label-free and selective biomolecular detection" Optics Express 25785: vol. 24, No. 22 | Oct. 31, 2016; pp. 12.

* cited by examiner

*Primary Examiner* — Jennifer Dunston
*Assistant Examiner* — Alexandra Rose Lippolis
(74) *Attorney, Agent, or Firm* — Allen, Dyer, Doppelt + Gilchrist, PA

(57) ABSTRACT

A method is for detecting a biomarker within a sample of blood. The method may include processing the sample of blood with a microfluidic blood plasma separator and a plasmonic array biosensor, and flowing the sample of blood over a sensing surface of the plasmonic array biosensor. The sensing surface of the plasmonic array biosensor may have an ssDNA aptamer against the biomarker. The method may further include binding the biomarker in the sample of blood to the ssDNA aptamer of the plasmonic array biosensor, and detecting the biomarker in the sample of blood based upon LSPR altering a reflected optical signal from the plasmonic array biosensor.

20 Claims, 18 Drawing Sheets

300

METHOD FOR DETECTING VIRUS USING SSDNA FUNCTIONALIZED SENSOR

GOVERNMENT RIGHTS

This invention was made with government support under grant ECCS-1808045 awarded by the National Science Foundation. The government has certain rights in the invention.

RELATED APPLICATION

This application is based upon prior filed copending Application No. 63/202,894 filed Jun. 29, 2021, the entire subject matter of which is incorporated herein by reference in its entirety.

TECHNICAL FIELD

The present disclosure relates to the field of biosensors, and, more particularly, to a biosensor for detecting a virus and related methods.

BACKGROUND

Viral infections are one of the topmost health concerns worldwide, especially those highly contagious that emerge from isolated geographical clusters and evolve rapidly into pandemics[1,2]. For instance, the Dengue virus (DENV), a member of the Flaviviridae family transmitted by female mosquitoes (*Aedes aegypti* or *Aedes albopictus*), produces a spectrum of clinical illnesses ranging from acute Dengue fever (DF), to deadly hemorrhagic fever (DHF) or the Dengue shock syndrome (DSS)[2-4]. The four DENV serotypes (DENV1, DENV2, DENV3, and DENV4) are a prevailing threat to almost half of the world's population, especially those at tropical latitudes where viral vectors are abundant[2]. In fact, it is estimated that 50 million DENV infections occur around the world each year and approximately 1% of these infections will require hospitalization as they develop into DHF or DSS[2]. Currently, there is no specific treatment for DENV infections, partly because the pathogenesis is not clearly understood[5-7]. Furthermore, efforts to develop and deploy an effective vaccine against all DENV serotypes has remained elusive, and the current approved vaccine (CYT-TVDV, Sanofi Pasteur) still has below 60% efficacy against the four DENV serotypes in children 2-17 years old[8,9]. Thus, the early detection followed by aggressive clinical intervention remains as one of the best ways to manage the infection and prevent chronic pathologies or death, and at the same time it becomes an strategic measure to contain the spread[1,2].

SUMMARY

Generally, a method is for detecting a biomarker within a sample of blood. The method may include processing the sample of blood with a microfluidic blood plasma separator, and flowing a portion of the blood plasma sample over a sensing surface of the plasmonic array biosensor. The sensing surface of the plasmonic array biosensor may have a high-affinity single stranded DNA (ssDNA) aptamer against the biomarker. The method may further include binding the biomarker in the sample of blood to the ssDNA aptamer of the plasmonic array biosensor, and detecting the biomarker in the sample of blood based upon a localized surface plasmon resonance (LSPR) altering a reflected optical signal from the plasmonic array biosensor.

In particular, the detection may comprise shining an optical signal into the plasmonic array biosensor and detecting the reflected optical signal. The method may also include flowing a buffer solution and the sample of blood through the microfluidic blood plasma separator until the reflected optical signal stabilizes. The method may further include increasing a flow of the sample of blood until plasma separation occurs to provide a plasma sample from the sample of blood, and performing the detection on the plasma sample. The method may further comprise incubating the plasma sample from the blood sample, and passing the plasma over the sensing surface of the plasmonic array biosensor. The method may comprise, subsequently to the passing, flushing the plasmonic array biosensor with the buffer solution.

More specifically, the biomarker may comprise a protein generated from at least one of a virus, a pathogen, a bacterium, and another microorganism. The biomarker may comprise at least one of a DENV1-NS1 protein, a DENV2-NS1 protein, or a Dengue virus protein. The method may further comprise reducing nonselective binding from proteins in the sample of blood based upon a passivation layer on the plasmonic array biosensor. For example, the method may further comprise detecting the biomarker in the sample of blood at a concentration less than 0.2 μg/mL.

Another aspect is directed to a method for making a plasmonic array biosensor for detecting a biomarker within a sample of blood. The method may include positioning a microfluidic blood plasma separator on a substrate of a plasmonic array biosensor to process the sample of blood, and functionalizing the plasmonic array biosensor with an ssDNA aptamer against the biomarker. A sensing surface of the plasmonic array biosensor may bind to the biomarker in the sample of blood, and the plasmonic array biosensor may detect the biomarker in the sample of blood based upon a LSPR signal.

More specifically, the method may further comprise passivating the sensing surface of the plasmonic array biosensor by at least forming a self-assembled monolayer. For example, the self-assembled monolayer may comprise a thiol-terminated 6-mercaptohexanol self-assembled monolayer.

Also, the microfluidic blood plasma separator may be removably clamped onto the substrate. The plasmonic array biosensor may comprise a hole-disc array. For example, the hole-disc array may have period of 0.5-0.6 μm, a diameter of 0.1-0.3 μm, and a relief depth of 0.2-0.4 μm. The method may further comprise forming a metallic back reflector on the plasmonic array biosensor. The method may further comprise forming a dielectric polymer base for the plasmonic array biosensor. The method may comprise forming a water proof membrane on the dielectric polymer base. For example, the water proof membrane may comprise aluminum oxide.

DETAILED DESCRIPTION

The present disclosure will now be described more fully hereinafter with reference to the accompanying drawings, in which several embodiments of the invention are shown. This present disclosure may, however, be embodied in many different forms and should not be construed as limited to the embodiments set forth herein. Rather, these embodiments are provided so that this disclosure will be thorough and complete, and will fully convey the scope of the present disclosure to those skilled in the art. Like numbers refer to like elements throughout.

The rapid spread of viral infections demands early detection strategies to minimize proliferation of the disease. Existing polymerase chain reaction (PCR) based viral detection techniques are slow and tedious, which poses technological limitations. Here, a plasmonic biosensor to detect Dengue virus is disclosed, which was chosen as a model virus, via its nonstructural protein NS1 biomarker. The sensor, which is functionalized with a synthetic single-stranded DNA oligonucleotide, provides high affinity towards the NS1 protein present in the virus genome. The present disclosure provides for the detection of the NS1 protein at a concentration of 0.1-10 μg/mL in bovine blood using an on-chip microfluidic plasma separator integrated with the plasmonic sensor, which covers the clinical threshold of 0.6 μg/mL of high risk of developing Dengue hemorrhagic fever. The present disclosure may demonstrate potential application of these microfluidic optical biosensors for early detection of wide range of viral infections, and may provide a rapid clinical diagnosis of infectious diseases directly from minimally processed biological samples at a point of care location.

Figure 1A:
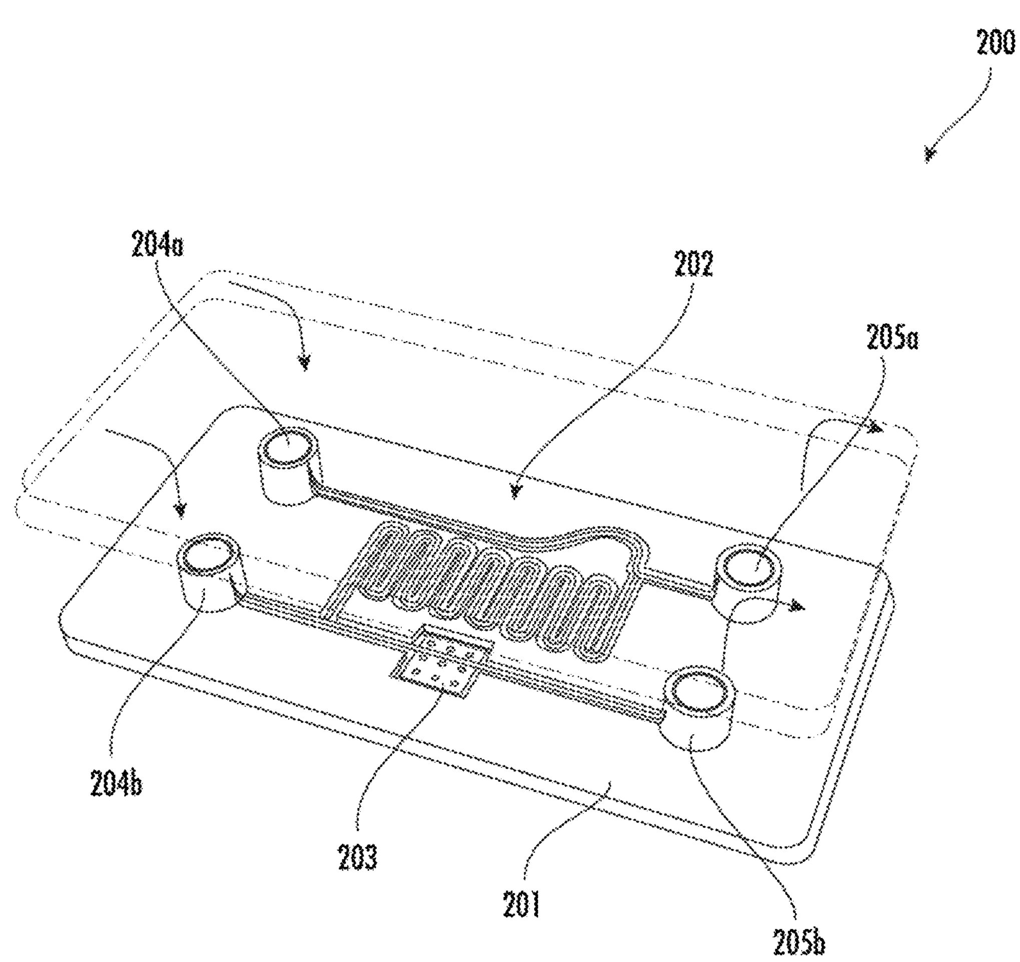
FIG. 1A is a schematic perspective view of an integrated biosensor, according to the present disclosure.
Figure 1B:
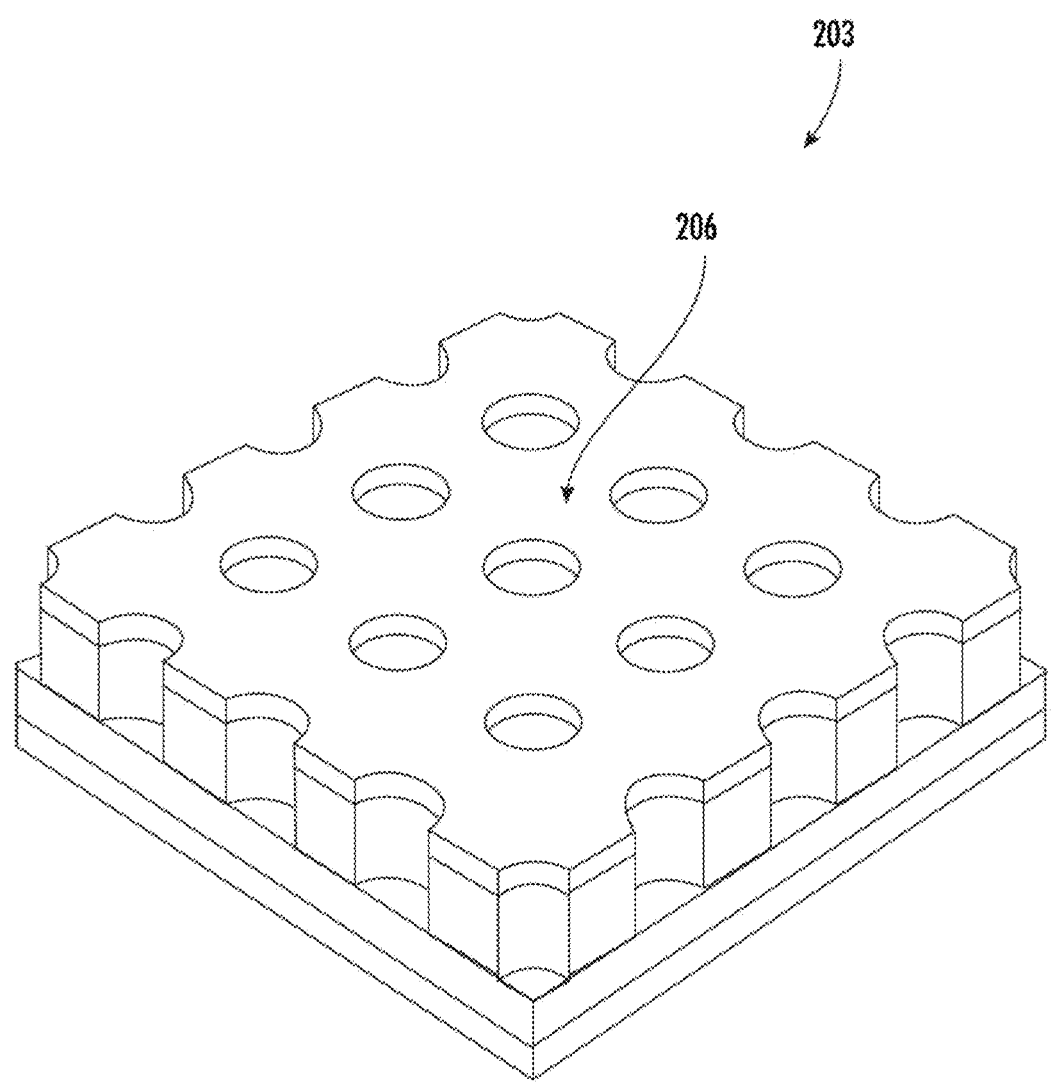
FIG. 1B is an enlarged schematic perspective view of the biosensor of FIG. 1A.
Figure 1C:
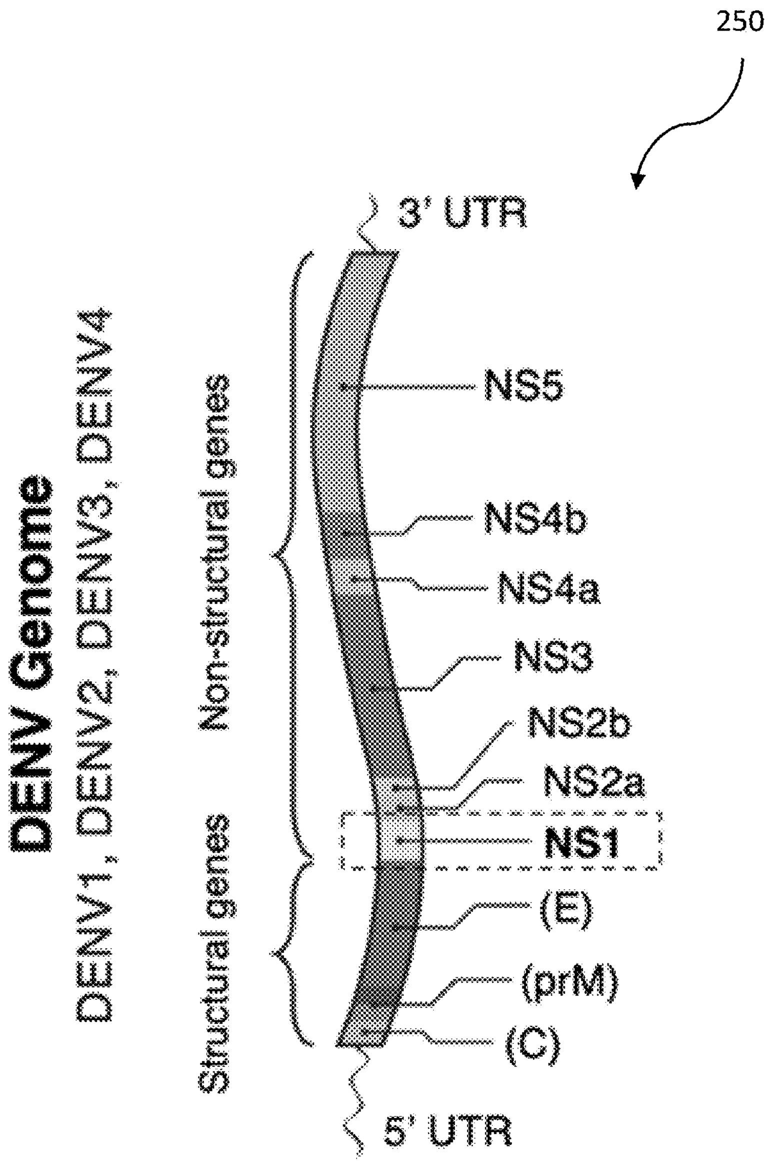
FIG. 1C is a schematic diagram of a dengue virus genome.
Figure 1D:
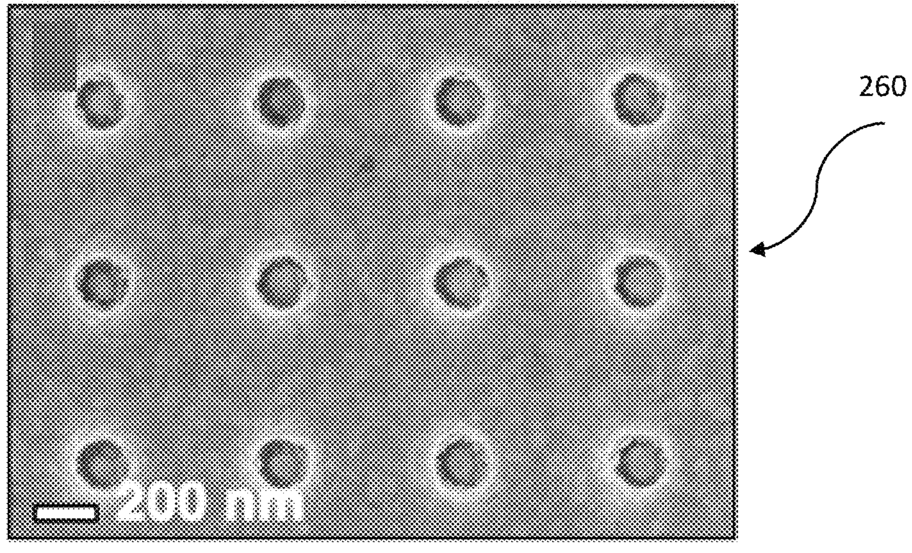
FIGS. 1D and 1E are scanning electron microscope top and cross-section images, respectively, of the biosensor of FIG. 1A.
Figure 1E:
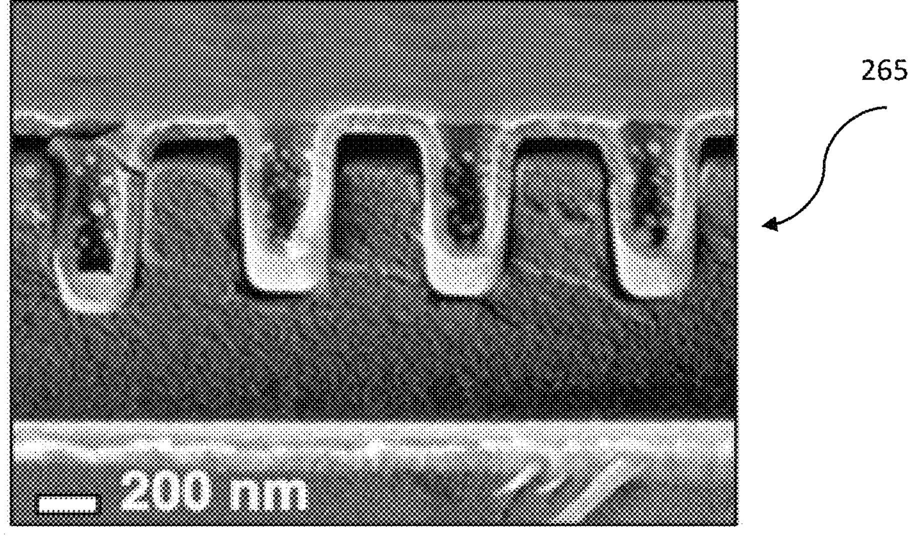
Figure 1F:
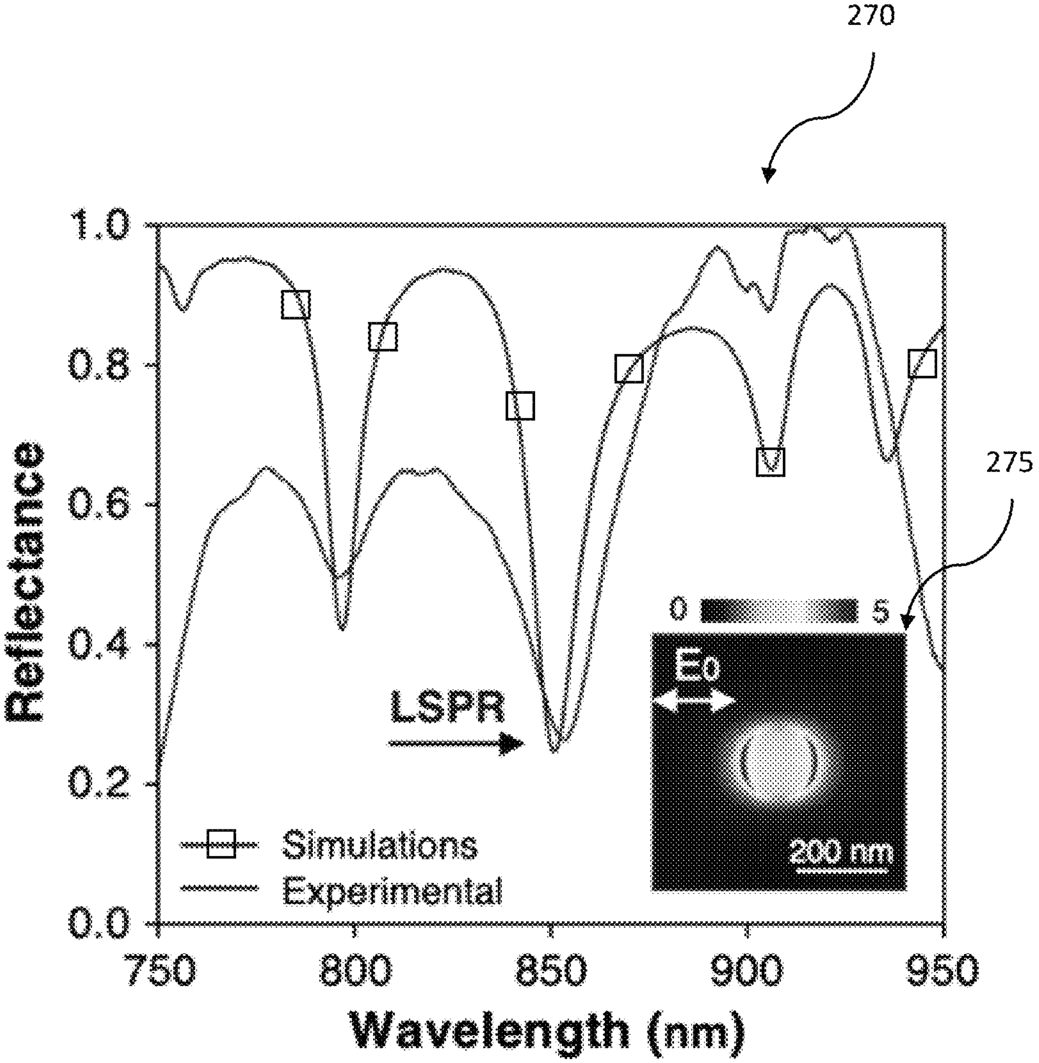
FIG. 1F is a diagram of the reflectance spectrum obtained experimentally and in a numerical simulation, according to the present disclosure.
Figure 1G:
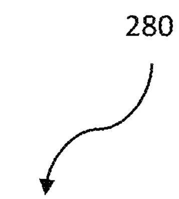
FIG. 1G is a schematic diagram of the biosensing workflow, according to the present disclosure.
Figure 1G:
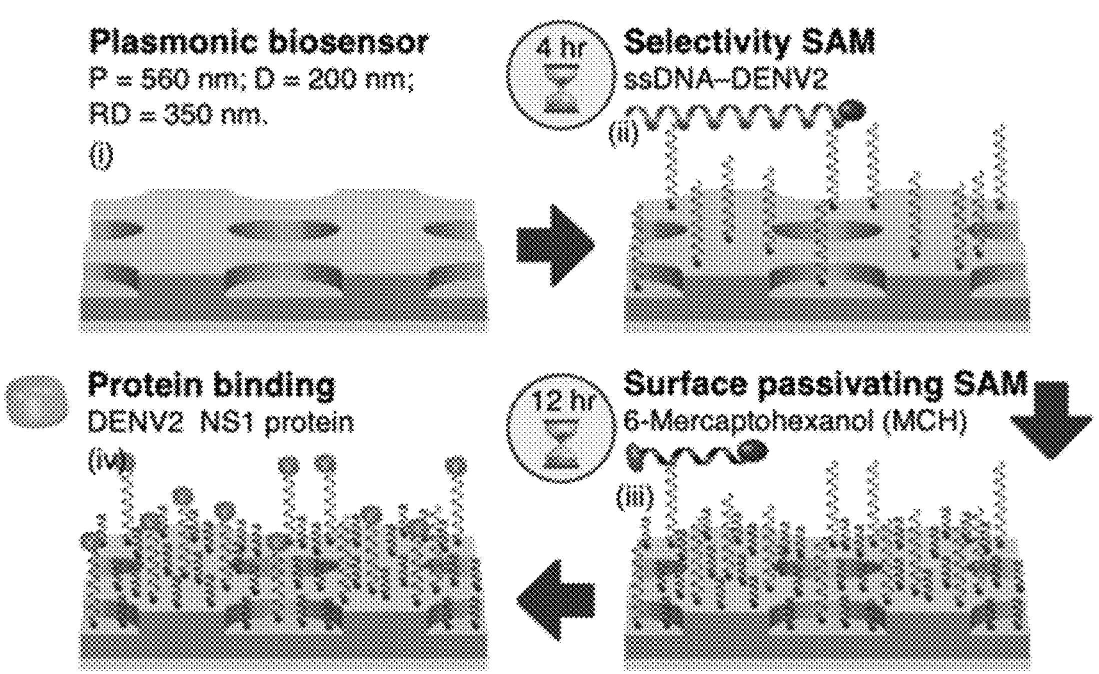

FIG. 1A: Integrated dengue virus biosensor comprises an in-line microfluidic blood plasma separator, and a cavity-coupled nanoimprinted plasmonic array. FIG. 1B shows the nanoimprinted plasmonic biosensor comprising a gold mirror (80 nm thick), a dielectric film spacer (~700 nm thick) embossed with a square array of holes, a conformal thin film of aluminum oxide layer (20 nm thick) as fluid barrier, and a thin film gold (30 nm thick). FIG. 1C shows the Dengue virus genome shared among the four DENV serotypes and comprising three structural (C, prM, and E) and seven nonstructural (NS) proteins, including NS1. FIGS. 1D-1E are scanning electron microscope images, top view (FIG. 1D) and cross section (FIG. 1E), of one representative nanoimprinted sensor. FIG. 1F shows a reflectance spectra obtained using FDTD simulations (square marked curve) and experimentally (solid curve). The inset of FIG. 1F represents the electric field enhancement obtained 5 nm above the circular hole at the LSPR. FIG. 1G shows a diagram 280 of biosensing workflow. (i) The sensors are batch prepared and properly cleaned prior to functionalization. (ii) Thiol-terminated ssDNA aptamer specific to nonstructural DENV2-NS1 protein binds covalently to the gold surface. This step requires incubation for 4 hours. (iii) Thiol-terminated 6-mercaptohexanol (MCH) self-assembly monolayer binds covalently to the empty surface area to block nonspecific binding and decrease protein fouling present in biological fluids. This process requires incubation for 12 hours. (iv) DENV2-NS1 protein detection is performed via aptamer binding, which produces a readable LSPR shift.

Figure 2A:
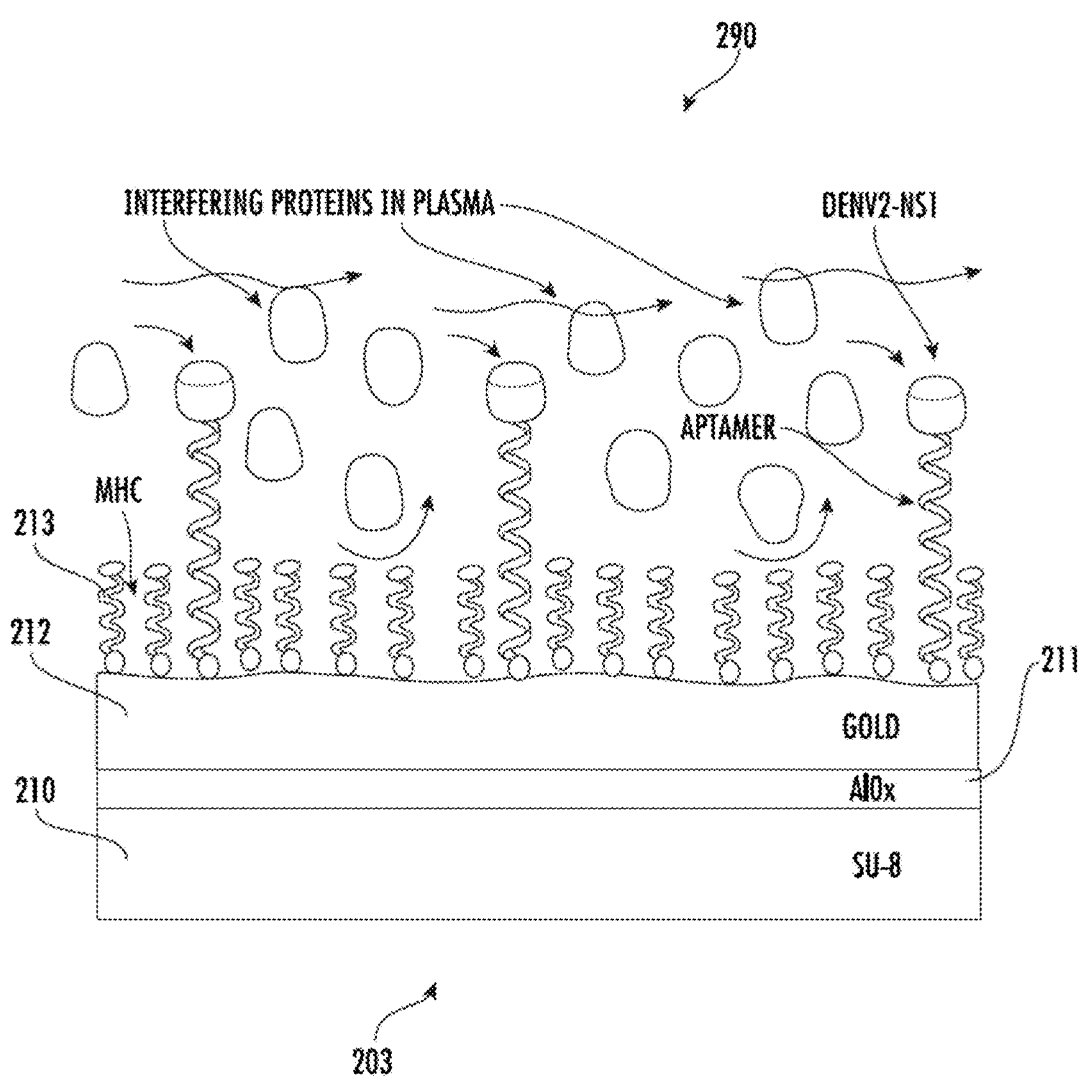
FIG. 2A is a schematic diagram of the biomarker being detected, according to the present disclosure.
Figure 2B:
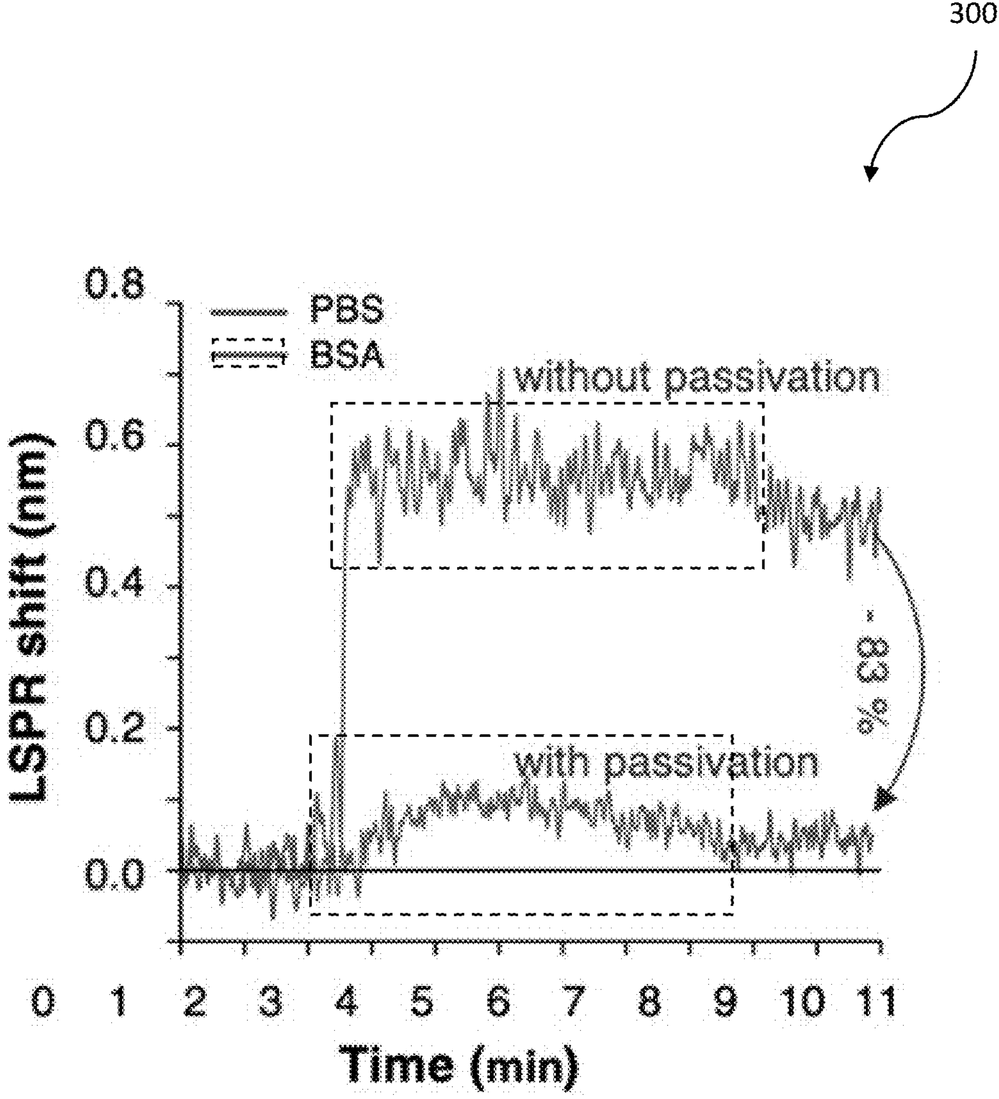
FIG. 2B is a diagram of bovine serum albumin (BSA) adsorption on a sensor with and without surface passivation, according to the present disclosure.
Figure 2C:
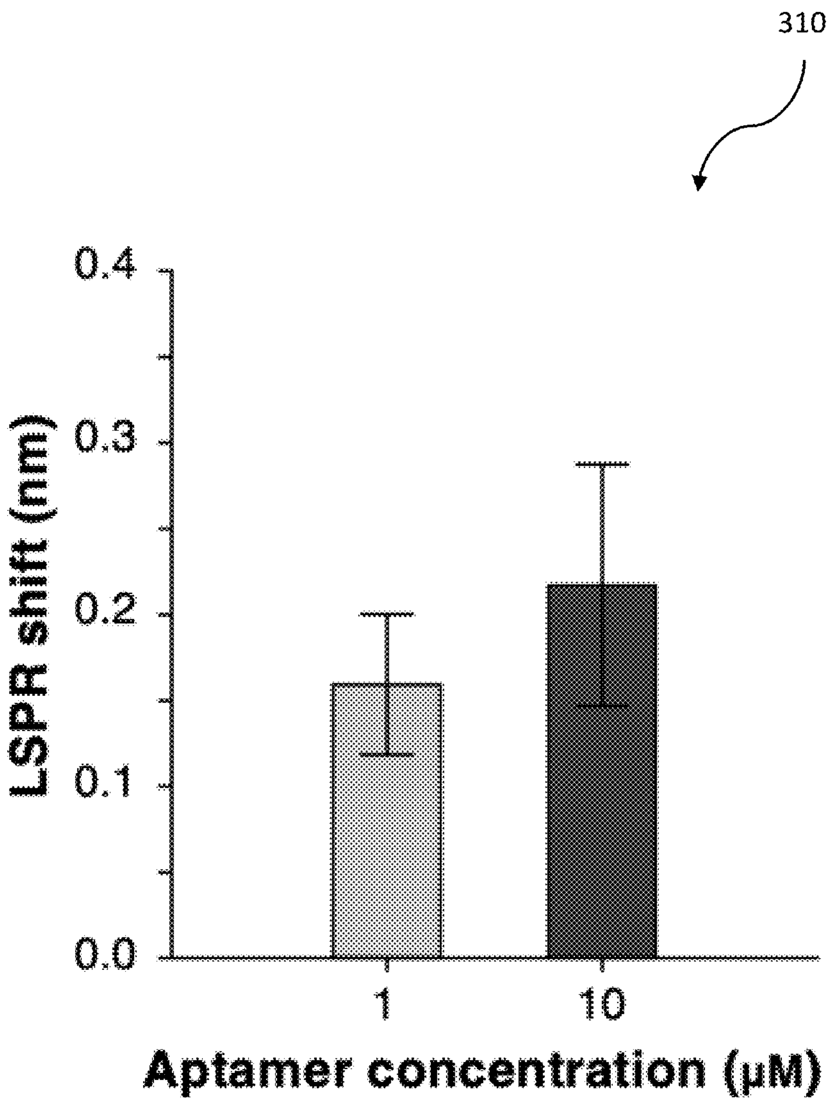
FIG. 2C is a diagram of aptamer concentration for functionalizing the sensor's surface, according to the present disclosure.
Figure 2D:
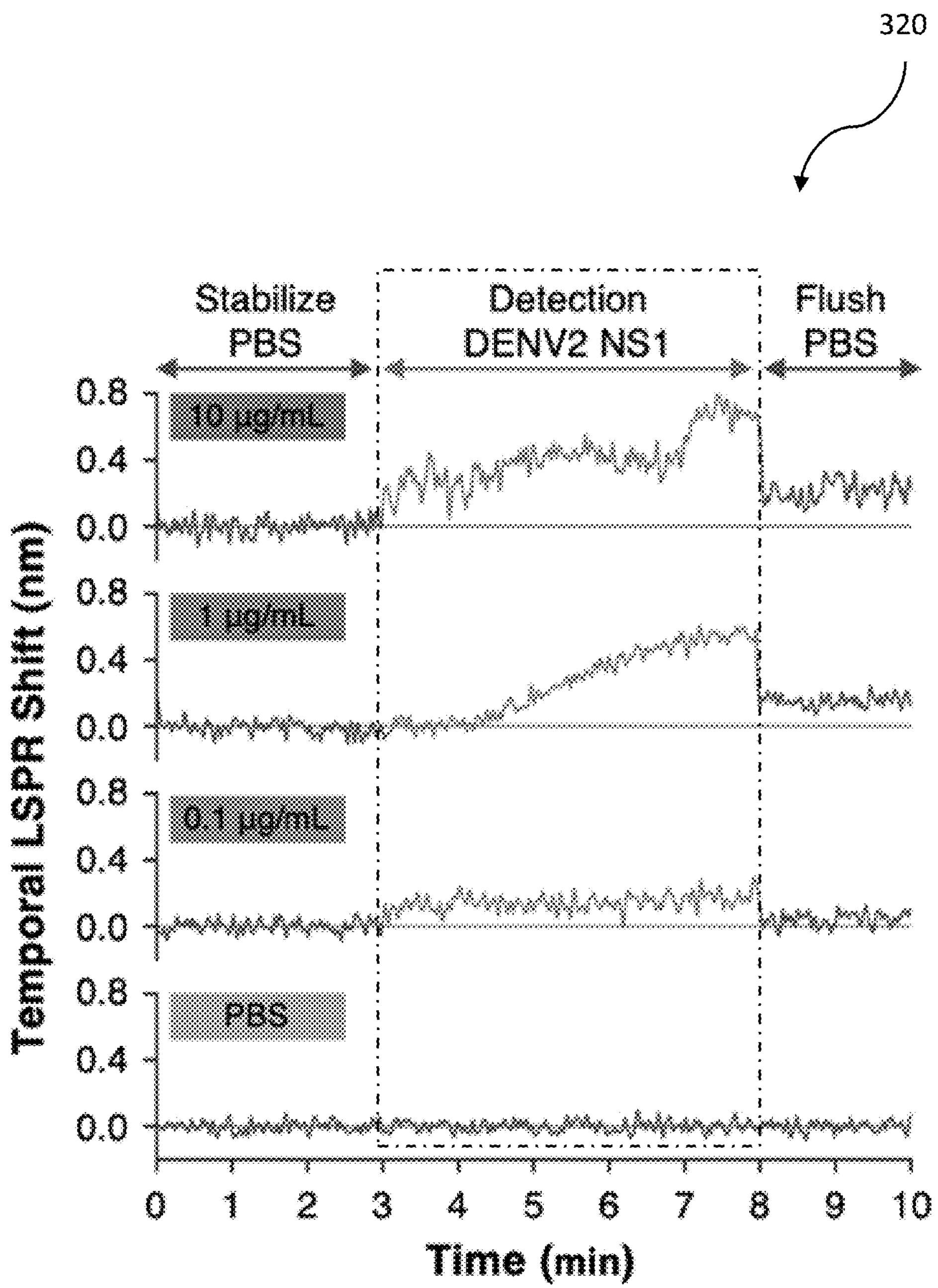
FIG. 2D is a diagram of LSPR time evolution for three DENV2-NS1 protein concentrations in phosphate buffer saline (PBS) and one control, according to the present disclosure.
Figure 2E:
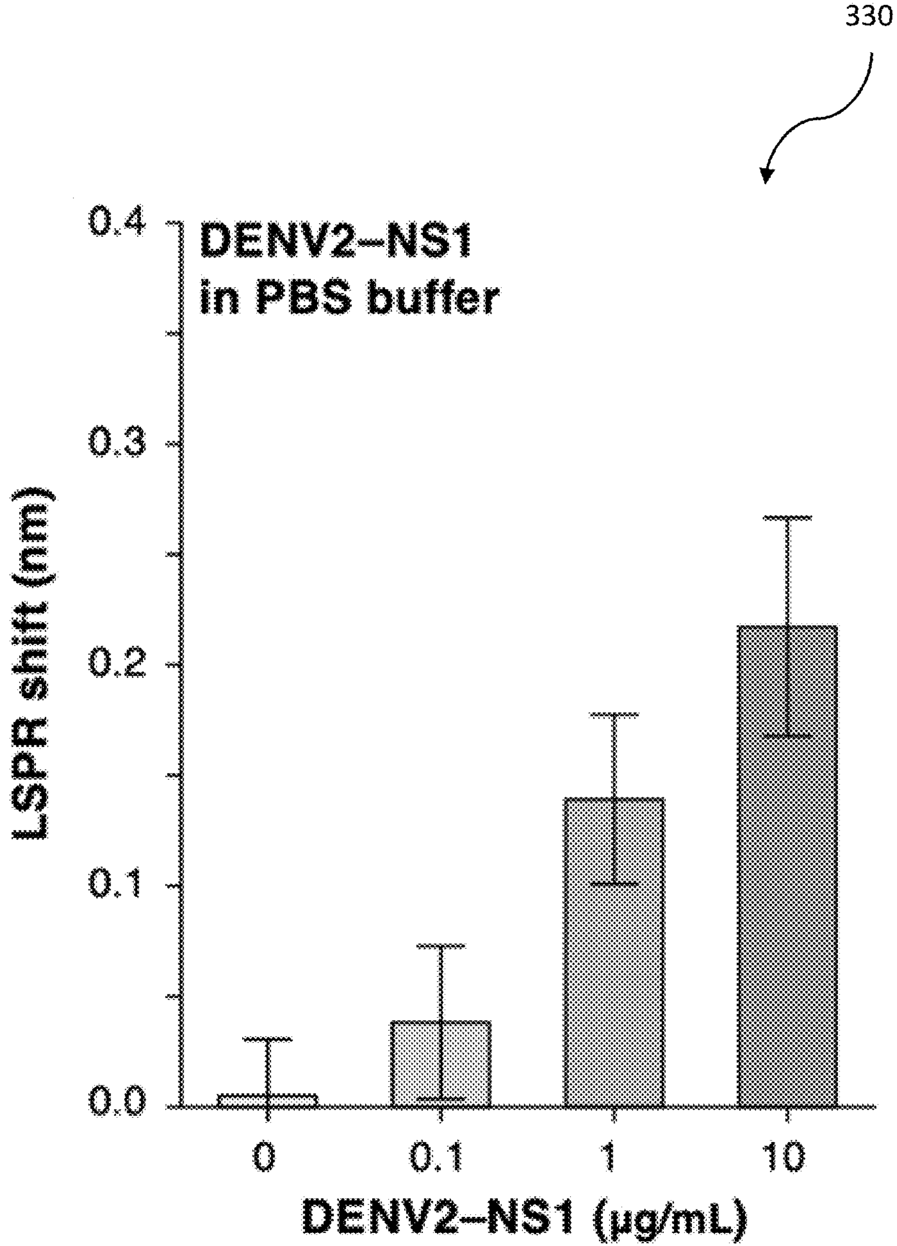
FIGS. 2E and 2F are diagrams of LSPR shift quantization in PBS and in PBS+BSA, respectively, according to the present disclosure.
Figure 2F:
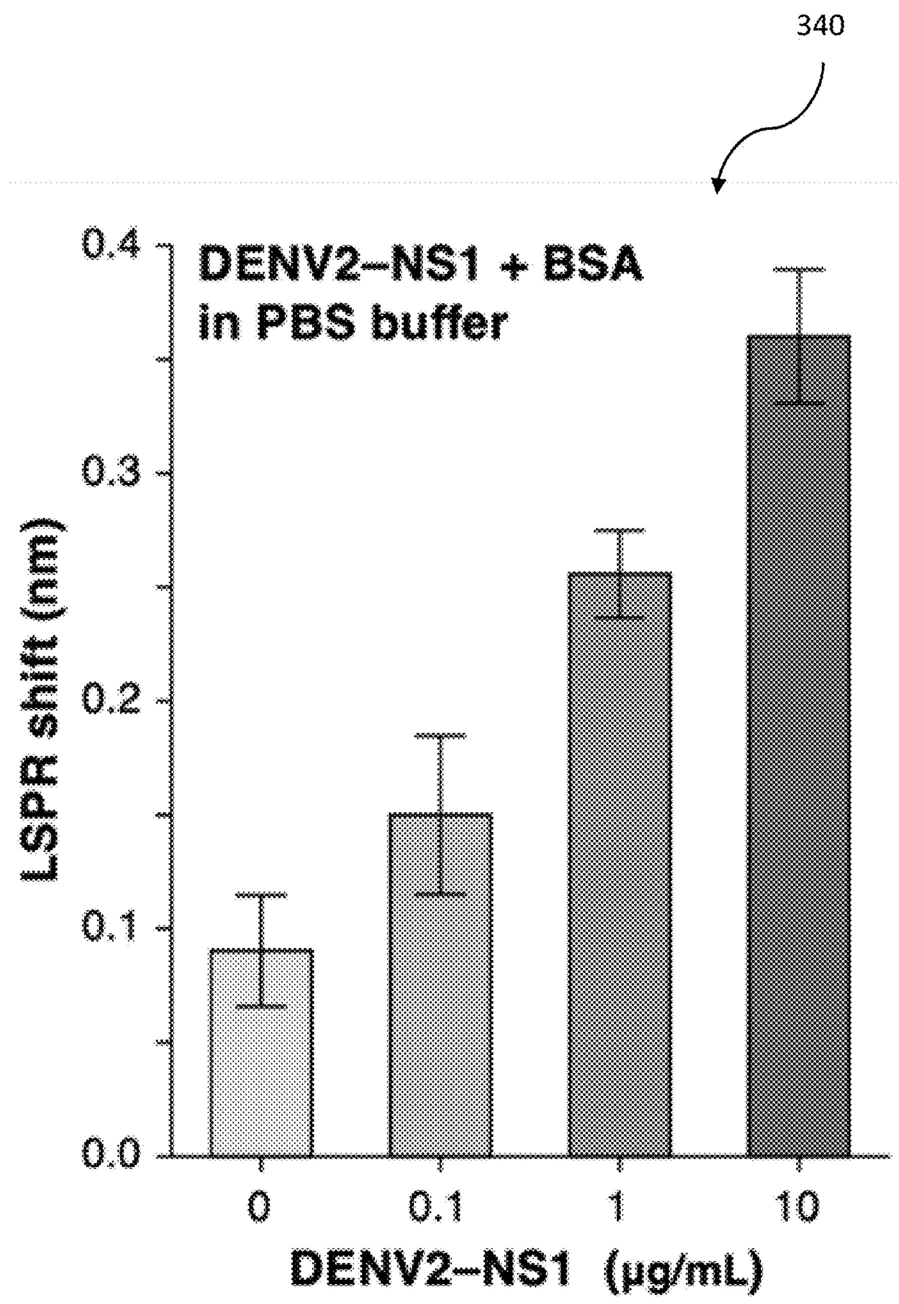

FIG. 2A shows a diagram 290 of biosensing from biological fluid. The surface passivation strategy decreases protein fouling while permitting the binding of the biomarker to the ssDNA aptamer. FIG. 2B shows a diagram 300 of thiol-terminated MCH surface passivation against BSA adsorption (100 μg/mL in PBS). Surface passivated sensor reduces up to 83% the sensor residual response with respect to its non-passivated counterpart. FIG. 2C shows a diagram 310 of biosensing with simultaneous passivation and functionalization. The sensors are functionalized with two aptamer concentrations (1 μM and 10 μM) and tested with same 10 μg/mL DENV2-NS1 concentration in PBS. FIG. 2D shows a diagram 320 of LSPR time evolution for three DENV2-NS1 protein concentrations (i.e. 0.1, 1, and 10 μg/mL) in PBS and one control (only PBS, or zero concentration). The sensorgrams show the time stamps at which the flow events were happening via the dashed box. The dashed box marks a detection period; before the dashed box marks the stabilizing period; and after the dashed box marks the flush period. FIG. 2E shows a diagram 330 for LSPR shift quantization of the four sensorgrams in FIG. 2D as a function of DENV2-NS1 protein concentration. FIG. 2F shows a diagram 340 of LSPR shift quantization of three DENV2-NS1 protein concentration in PBS solution with additional 100 μg/mL BSA concentration, and control sample (only PBS+BSA, or zero concentration). Error bars are the standard deviation from the mean.

Figure 3:
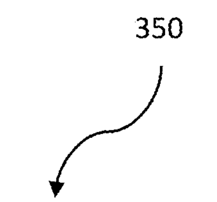
FIG. 3 is a diagram of detection of DENV1 and DENV2 NS1 proteins in PBS+BSA and a control (PBS+BSA), according to the present disclosure.
Figure 3:
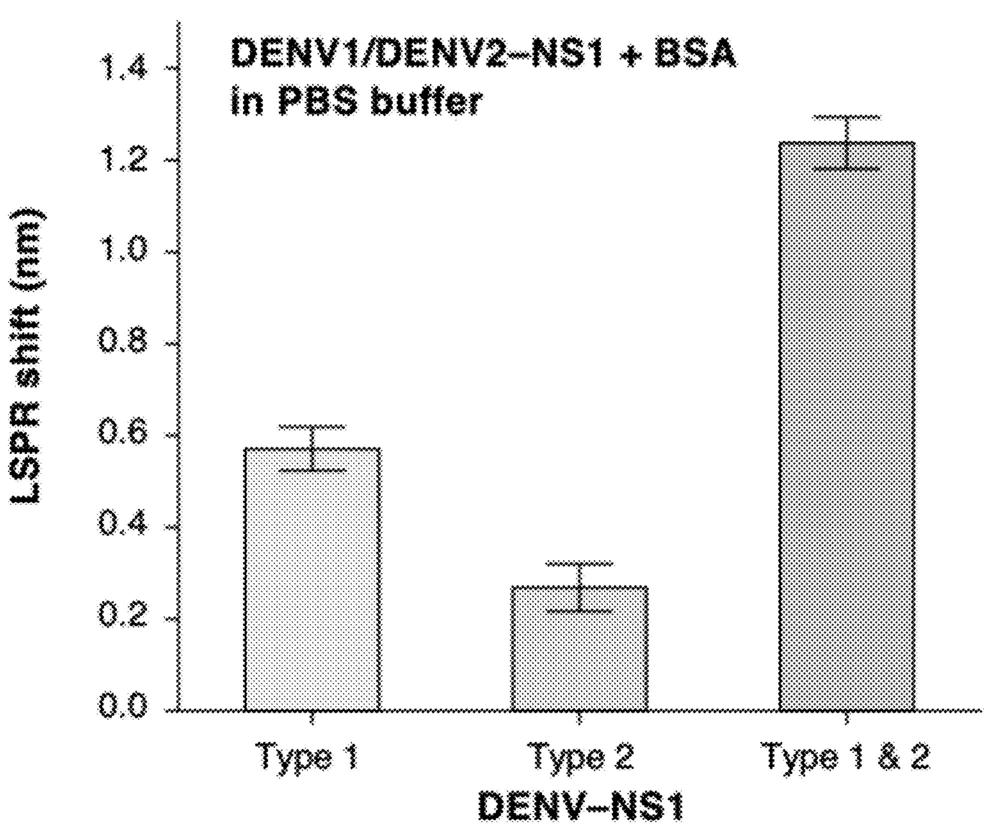

FIG. 3 shows a diagram 350 of detection of DENV1 and DENV2 NS1 proteins in PBS. The close genetic match of the NS1 protein between the DENV1 and DENV2 (71.67%) leads to finite LSPR shift when testing DENV1 and DENV2 separate or DENV1+DENV2 combined. Error bars are the standard deviation from the mean.

Figure 4A:
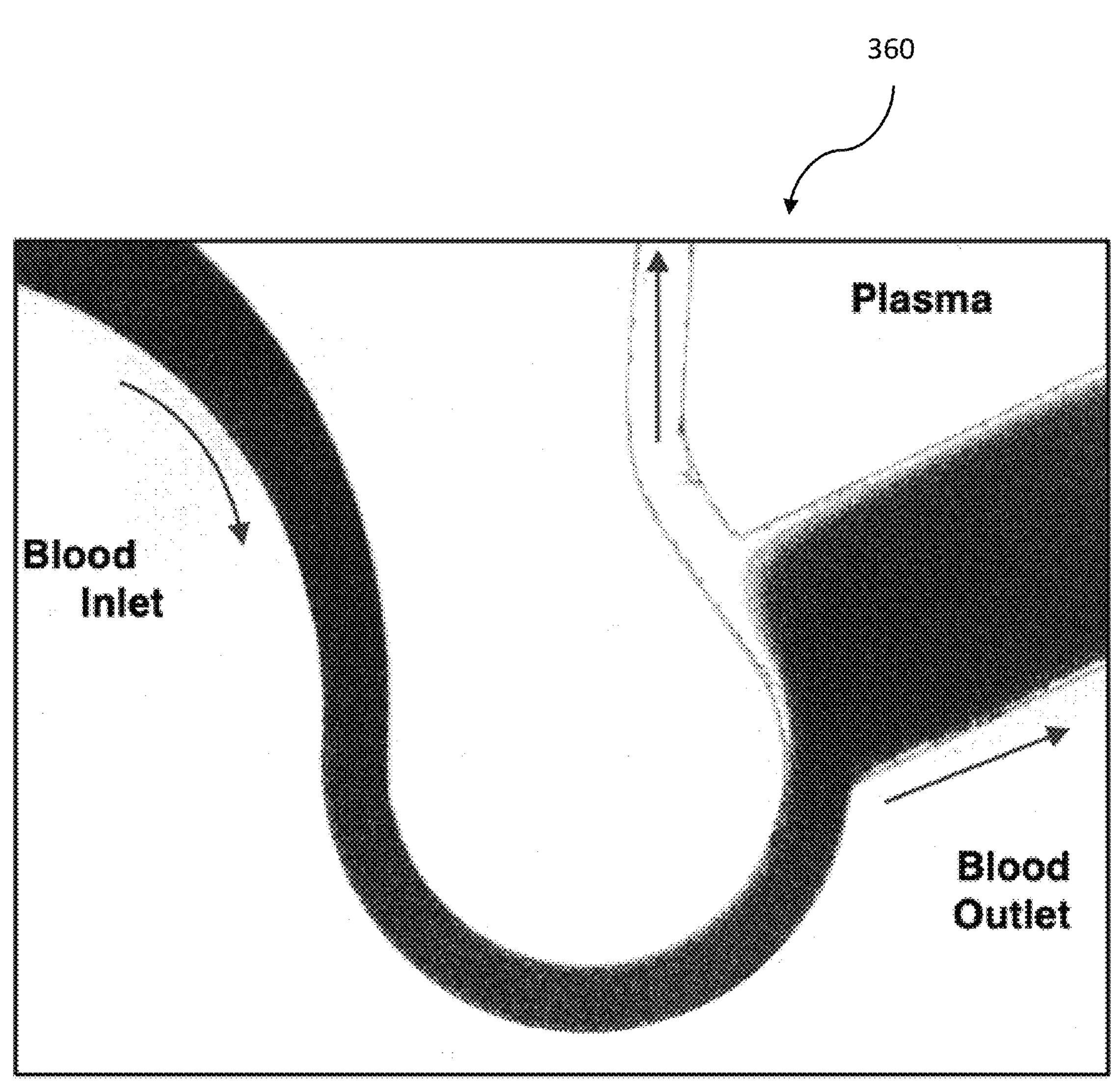
FIG. 4A is a microscope image of blood plasma separation using the integrated microfluidic device, according to the present disclosure.
Figure 4B:
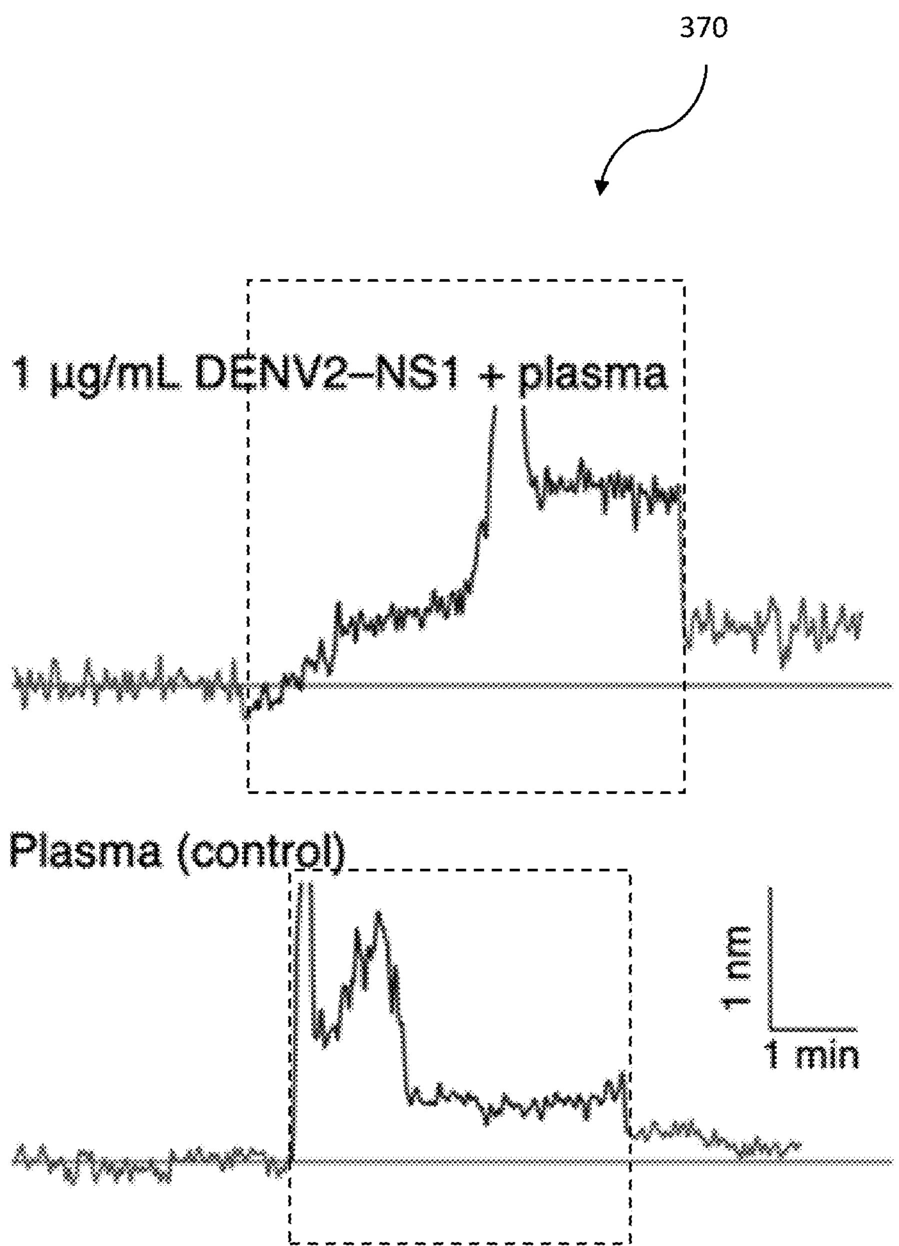
FIG. 4B is a diagram of biosensing from blood, according to the present disclosure.
Figure 4C:
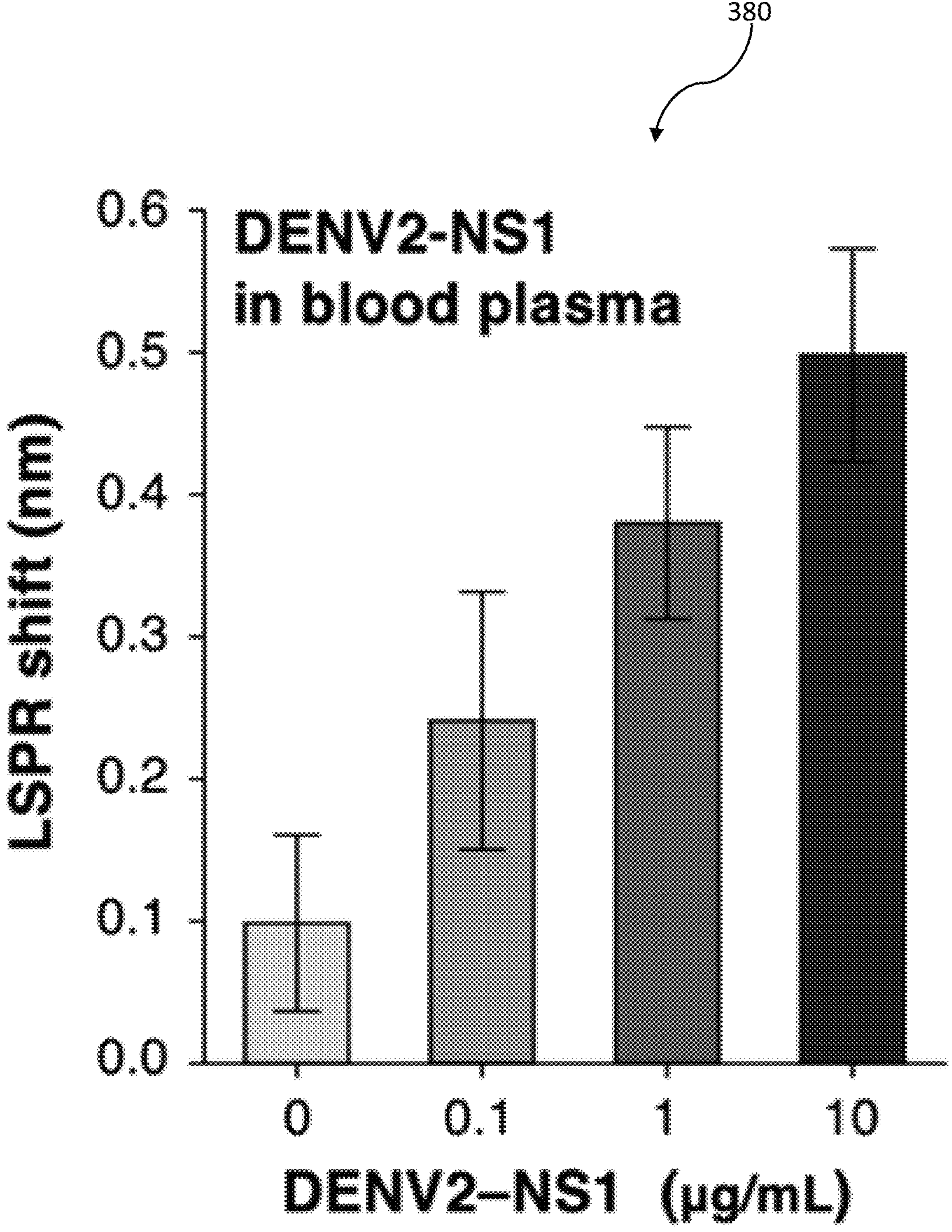
FIG. 4C is a diagram of DENV2-NS1 protein detection at different concentrations in blood and one control, according to the present disclosure.
Figure 5:
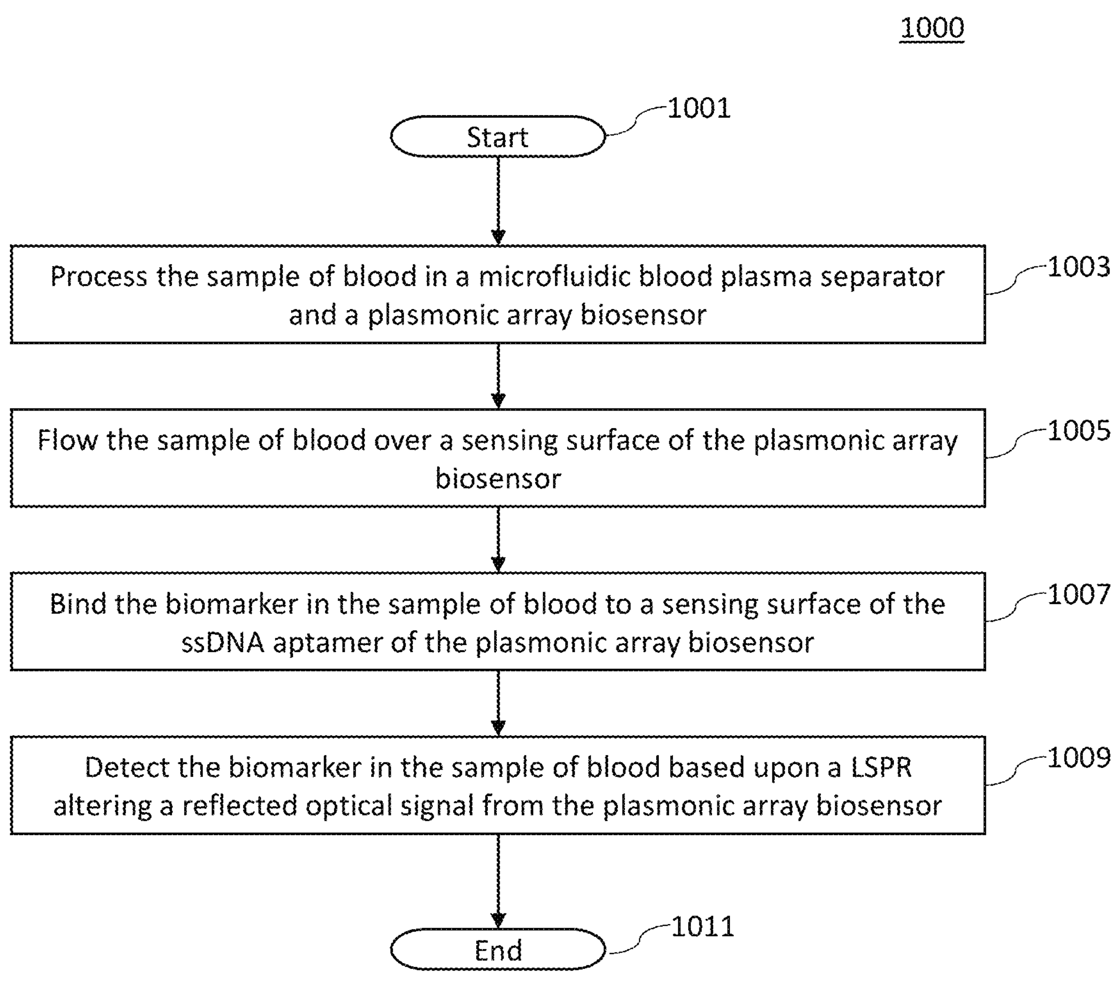
FIG. 5 is a flowchart of a method for detecting a virus in a sample of blood, according to the present disclosure.

FIG. 4A shows a microscope photograph image 360 of the blood plasma separation during operation. FIG. 4B shows a diagram 370 of two representative sensorgrams during the biosensing demonstration from blood. First a baseline is stablished by flowing PBS first, then plasma separation is started followed by an incubation time (typ. 3 min) and finalized with PBS flush. FIG. 4C shows a diagram 380 of DENV2-NS1 protein detection at different concentration (0.1, 1, and 10 μg/mL) in blood and one control (just blood). This biosensing strategy demonstrates biomarker detection from complex biological fluids, such as blood plasma. Error bars are the standard deviation from the mean.

Viral infections, such as DENV, are diagnosed using antibody, protein biomarkers, or messenger ribonucleic acid (mRNA) from a biological sample. On one hand, the enzyme-linked immunosorbent assay (ELISA) is the clinical diagnostic gold standard for seral antibodies or proteins detection, which is an indirect approach to identify an active or past viral infection[10,11]. On the other hand, the reverse transcriptase polymerase chain reaction (RT-PCR) specifically targets viral mRNA strands with high accuracy, which is ideal for the diagnosis of active viral infections with specific genome specificity. However, the cost of a time consuming process, the dedicated infrastructure, and the extensive sample preparation in both cases restricts the proliferation beyond commercial laboratories and academic environments. Alternative label-free affinity biosensors promise to develop assays for the rapid diagnosis of pathogenetic biomarkers, for example those based on localized surface plasmon (LSP)[14,15]. These devices are extremely sensitive due to the subwavelength electric field confinement produced by the LSP at resonance which makes them ideal for small biomolecule detections. When properly functionalized with an affinity recognition layer, these sensors can detect minute concentrations of analyte down to the picomolar to femtomolar concentrations.

In the present disclosure, a cavity-coupled plasmonic biosensor 200 integrated with a microfluidic blood plasma separator[16-18] may detect the DENV biomarker directly from blood as schematically is shown in FIG. 1A. The cavity coupling improves the quality factor Q (bandwidth, ΛΛ) of the LSPR while nanoimprinting based patterning ensures a deterministic resonance ($\lambda_R$)[16,19]. Both of these attributes were previously shortcomings and prevented the commercial development of plasmonic sensors.

In order to make it target specific, the plasmonic biosensor is functionalized with a ssDNA aptamer against the nonstructural NS1 protein from DENV2 serotype, (diagram 250 FIG. 1C). Aptamers are synthetic short single-stranded nucleic acids which are specifically designed to bind, with high genetic selectivity, a myriad of targets, from ions, small molecules and proteins to supramolecular complexes[20,21]. They outperform antibodies, typically used in affinity layers in biosensing, in many different ways[22]. For example, single-stranded DNA (ssDNA) aptamers are chemically synthesized using the systematic evolution of ligands by exponential enrichment (SELEX) method to bind the target with high affinity[23,24], and cloned afterwards. This makes the aptamer production process cost-effective for highly reproducible biosensing platforms as no living animal model is needed for the production[25,26]. In addition, the present disclosure includes a surface passivation scheme based on thiol-terminated MCH self-assembled monolayer to minimize nonselective binding from proteins present in biological fluids, such as blood plasma. With this genetically modified sensor design, the present disclosure discloses the detection of NS1 protein from DENV2 at a concentration of 0.1-10 μg/mL in bovine blood using a plasma separating microfluidic chip integrated with this plasmonic biosensor. This concentration range covers the clinical threshold of 0.6 μg/mL for predicting high risk of developing DHF in DENY infected patients[11,27].

Results: Plasmonic Biosensor

LSP oscillations are supported at the interface between dielectric and subwavelength metallic structures. The LSPR is inherently determined by the geometrical configuration, materials, and the surrounding dielectric permittivity. Any modification to these parameters induces a resonance shift, however without any selectivity. That means two similar biomolecules when attached to the metallic interface impart same resonance shifts, making them indistinguishable. Hence, it is essential to incorporate an affinity layer against the target biomarker to produce a selective LSPR shift upon analyte binding to enable label-free affinity-based plasmonic biosensing.

The plasmonic sensor is formed by hybridizing the LSP with an asymmetric Fabry-Perot cavity resonator[17,19,28]. The plasmonic nanostructure, unlike typical one metallic element, is composed of two complementary elements, hole/disk, of period/diameter of 560/200 nm and separated by 350 nm relief depth. The pattern is thermally embossed on UV curable epoxy SU-8 and coated with 30 nm of gold (See FIG. 1B). Further, the complementary hole/disk array is far-field coupled with the photonic cavity formed by an optically thick (100 nm) gold back reflector separated from the plasmonic nanostructure by a thick SU-8 spacer film (typically 700 nm). In applications where the plasmonic device is submerged in solvents, including water, for prolonged periods of times leads to SU-8 swelling[29], which could add finite cavity thickness variations observed in spurious LSPR shift. In order to prevent this detrimental effect, a conformal 20 nm aluminum oxide membrane is grown on the polymeric nanohole array prior to metal evaporation to prevent water diffusion into the epoxy matrix. FIG. 1B depicts the schematic representation of this system and the corresponding scanning electron microscope (SEM) image of one representative device with cavity thickness of ~700 nm is shown in images 260, 265 of FIGS. 1C-1D. Cavity-coupled plasmonic systems support hybridized LSP oscillation modes in the top metallic nanostructure that, when coupled with a back metallic reflector, form an asymmetric photonic cavity. Light coupled to this cavity produces Fabry-Perot resonant modes and, when overlapped in space and time with LSP, generates hybrid LSP modes[19]. Such hybrid LSP modes offer robustness against fabrication tolerances due to the weak space-time coupling between the cavity and LSP modes. FIG. 1F shows the reflection spectra obtained using finite difference time domain (FDTD) simulations (i.e. Q factor of 53) compared with that obtained experimentally (i.e. Q factor of 37) when immersed in aqueous solution (n=1.333). At resonance (LSPR~850 nm), the hole/disk array supports a plasmonic resonance (inset 275 in diagram 270 of FIG. 1F) which is extremely sensitive to changes in the surrounding medium, resulting in a measurable shift in the resonance frequency.

Target Specific Viral Genome Detection

Nonstructural NS1 glycoprotein forms part of the genetic code of all the Flaviviridae virus family, such as the four serotypes of the DENV, the Japanese encephalitis virus, Yellow fever virus, West Nile virus, tick-borne Encephalitis virus, and Zika virus[30-32]. FIG. 1C shows the DENV genome, which is not different from the general Flaviviridae virus family[32]. However, such a genomic similarity does not translate to a genetic material homogeneity. For example, only 23% of the protein genome is conserved among these virus genera. In addition, DENV2 shares 71.44% with DENV1, 71.64% with DENV3, 68.82% with DENV4, 55.44% with Zika virus, 51.96% with West Nile virus and 45.46% with Yellow fever virus[32,33]. NS1 proteins, a constituent of the DENV genome, plays an important role in the virus replication process, and is secreted into the blood stream by the infected cells, thus it becomes a representative biomarker for the identification of the infection[34,35]. It was demonstrated that high levels in acute-phase serum samples correlated with high risk of developing DHF[11,27]. Hence, detection directly from the blood, or plasma, is essential in order to avoid fatalities.

To target specific detection, the sensor is functionalized with ssDNA aptamer to detect NS1 protein directly from blood. However, detection from minimally processed and unfiltered biological samples in general is challenging due to the protein adsorption on sensor surface. The high protein content in blood plasma tends to electrostatically accumulate on the negatively charged gold surface producing a spurious biofilm accumulation leading to an uncontrolled background masking the positive binding of the target biomarker. In order to address such a protein fouling, the present disclosure implements a surface passivation based on thiol-terminated MCH self-assembled monolayer, which is a typical surface passivating strategy for gold-based biosensors[21,36,37]. The functionalization and biosensing workflow are graphically represented in diagram 280 of FIG. 1G. The plasmonic substrates were batch nanoimprinted (FIG. 1G-i), functionalized with commercially available thiol-terminated ssDNA aptamer against the NS1 protein from DENV2 (DENV2-NS1) serotype (Base Pair Biotechnologies Inc.) (FIG. 1G-ii), followed by surface MCH passivation (FIG. 1G-iii), and finally NS1 protein binding detection using optical reflection spectroscopy and subsequent quantization by LSPR shift (FIG. 1G-iv). This specialized surface functionalization and passivation, enabled detection of antigen even in presence of high protein content in the biological sample as can be seen in diagram 290 of FIG. 2A. The sensor passivation was characterized first using 100 μg/mL BSA in PBS as a model for non-specific interfering protein contained in biological samples.

Two non-functionalized plasmonic substrates were prepared with and without surface passivation. This PBS+BSA solution was flowed using a microfluidic chip placed on top of the plasmonic substrate and secured with an acrylic fixture. First, the PBS flows in the microfluidic channel to bring the sensor to a stable state determining the baseline. Then, the PBS+BSA solution flows for five minutes and then flushed away with PBS to remove poorly adhered BSA on the gold surface. Protein adsorption and selective biding in the subsequent biosensing demonstrations, is gauged using the LSPR shift with respect to the baseline. In the plasmonic substrate without passivation, BSA accumulates rapidly within half a minute and remain constant independent of the continuous BSA flow, which is a sign of surface saturation. The flow of PBS solution flushes any poorly adhered BSA, but the residual LSPR shift (0.497±0.028 nm) denotes a considerable remaining protein adhesion to the substrate, see diagram 300 of FIG. 2B. In contrast, the BSA minimally affects the surface passivated substrate observed in the slower sensor response and the small residual LSPR shift (0.083±0.018 nm) after PBS flush. This strategy achieves about 83% reduction in the residual LSPR shift. After confirming the surface passivation implementation, the plasmonic biosensor with simultaneous ssDNA aptamer functionalization and surface passivation was tested. Two sensors were functionalized with 1 and 10 μM ssDNA aptamer concentration and 10 μg/mL purified DENV2-NS1 protein in PBS buffer was flowed in the same pattern as described in the previous surface passivation characterization. FIG. 2C includes a diagram 310, which shows the LSPR shift, which confirms the sensor binds the biomarker at two strengths commensurate with the surface coverage of the ssDNA aptamer; 10 μM ssDNA aptamer concentration was employed in all the subsequent biosensing demonstrations.

Detection in PBS

The first detection demonstration is performed in PBS solution where purified DENV2-NS1 protein was spiked at different known concentrations. The purpose of this characterization is to evaluate the binding capability to detect the target biomarker within the clinically relevant concentration for high risk DHF development (0.6 μg/mL)[11,27]. A batch of sensors were fabricated, functionalized and surface passivated. Using the integrated microfluidics system, each sensor was exposed to different DENV2-NS1 protein concentrations, 0.1, 1 and 10 μg/mL including a control solution (in this case just PBS). The sensors were first stabilized with PBS running buffer, then the PBS+DENV2-NS1 solution flowed for five minutes followed by PBS flush, while continuously collecting the reflection spectra at each second interval using a spectrometer automated with a customized LabVIEW (National Instruments) graphic user interface. Typical time evolution of the LSPR shift can be observed in diagram 320 of FIG. 2D.

The results of this characterization are summarized in diagram 330 of FIG. 2E where the LSPR shift is plotted as a function of DENV2-NS1 protein concentration. The fact that the LSPR shift is technically zero for the control solution validates the effect of the aluminum oxide passivating layer that prevents SU-8 swelling when exposed to aqueous solution for the 10-minute period. In addition, the low LSPR shift for 0.1 μg/mL concentration (0.038±0.035 nm) suggests limit of detection in this range. This demonstration shows a promising performance and paves the path for detection of DENV2-NS1 from real biological samples containing elevated concentration of proteins.

Detection from PBS+BSA

In order to assess the device performance in artificial sample conditions, i.e. saline solution with high protein content (BSA) and the target biomarker, the same experiment was repeated, but 100 μg/mL of BSA was added into the PBS buffer. The sensors were batch fabricated, functionalized and surface passivated. FIG. 2F includes a diagram 340, which summarizes the LSPR shift with respect to DENV2-NS1 protein. It is observed that the control solution, PBS+BSA only, has a small background (0.090±0.024 nm) such as that seen during the surface passivation test, see FIG. 2B. However, the LSPR shift as a function of DENV-NS1 protein concentration varies in much the same way than the case without BSA with sensor response of (0.150±0.035 nm) for the smallest DENV2-NS1 concentration. Such a demonstration confirms that this biosensing strategy has the potential to detect the target biomarker even in environments where other non-specific biomolecule binding, BSA in this case, could mask the response. The ssDNA aptamer used was designed against DENV2-NS1, but due to its 71.46% overlap with DENV1-NS1 genome the biosensor produced a finite response. FIG. 3 includes a diagram 350 showing the LSPR shift response from three PBS+BSA solutions containing 10 μg/mL of DENV1-NS1, 10 μg/mL of DENV2-NS1 and a mix of 10 μg/mL of each. Henceforth, it is expected that with further aptamer optimization guided by the diversity of the NS1 genetic code, it would be possible to detect DENV1 and DENV2, along others Flaviviridae with high specificity.

Direct Detection from the Blood

Ultimately, a biosensor capable of performing biomarker detection from minimally prepared blood samples is the key for the point-of-care clinical diagnostics and other applications that require portability. In order to demonstrate the feasibility of performing DENV2 detection using the circulating NS1 protein biomarker directly from bovine blood, the plasmonic biosensor was integrated with an on-chip microfluidic plasma separator[18], see FIG. 1A. This microfluidic chip uses a series of biophysical and hydrodynamical effects to generate a cell-free region as the result of cell migration and inertial focusing at the bifurcation of an asymmetric flow resistance paths with ratio of at least 2.5:1[38], where large cells such as red and white blood cells and platelets are deviated towards the low resistance path and cell-free plasma is collected in on the opposite[39-41]. The hybrid microfluidic-plasmonic chip was fabricated using standard photolithography and nanoimprinting techniques. In addition, the chip was held secured to the gold surface using a customized acrylic clamp. This way, the microfluidic chip is removed, cleaned and reused multiple times. The samples were batch fabricated, surface functionalized and passivated following the same method described above. Bovine whole blood (~35% hematocrit (HCT)) was prepared by spiking a deterministic concentration of DENV2-NS1 protein (0.1, 1, and 10 μg/mL) and control in PBS solution which produced blood samples with ~22.3% HCT. Blood samples with lower HCT perform better than high hematocrit content blood samples using these type of devices, especially in the low flow regime preventing the non-covalent bonded microfluidic chip from delamination[39].

Detection directly from blood following this scheme requires four steps. In the first step, PBS and blood flows at low speed at the same time to fill the channels with solution. Once the reflected optical signal is stabilized, the PBS channel closes meanwhile the blood flow increases until plasma separation occurs within the first two minutes, see microscope photograph image 360 of FIG. 4A. Once cell-free plasma flows on the active sensing region, the blood flow is stopped and kept off for another 3 minutes to incubate the plasma sample. Then, the PBS channels is open to flush the plasma and other proteins off the active region. FIG. 4B shows a diagram 370 of two LSPR chronograms, non-boxed regions are the PBS flow events and the dashed box region correspond to the plasma separation and detection. Spikes in the LSPR are observed mainly due to event related to remnant blood cells, refractive index gradients, loss of LSPR tracking, or the reflectance spectra flattens, but not biomarker binding. However, flushing with PBS solution allows for the reflectance spectra to recover to the baseline state but with an LSPR shift gained by the binding of the biomarker. As expected, the control sample produces a small background in the same range that in the previous biosensing experiment (0.099±0.024 nm). Nevertheless, the DENV2-NS1 protein was clearly differentiated at different concentrations, see diagram 380 of FIG. 4C. In addition, similar limit of detection is observed (0.1 μg/mL) still within the clinical threshold for high risk of DHF development (0.6 μg/mL).

Other methods of DENV detection mostly use immunoassay approaches—the use of antibodies as the affinity layer. For example, the detection of DENV E-protein (see FIG. 1C) in buffer[42], Immunoglobulin M, as the immune system response to DENV infection, in diluted human serum[43], and NS1 protein in diluted human blood plasma[44] were performed using the surface plasmon resonance (SPR) method, with detection limits in the femtomolar rage for DENV E-protein in buffer[42]. Other optical methods such as luminescence of quantum dots conjugated with gold nanoparticle via ssDNA aptamers detect purified DENV DNA complementary strands at femtomolar concentrations in buffer[45]. Unlike other demonstrations, the present disclosure shows the use of a hybrid microfluidic-plasmonic device as a promising technique for the rapid sample preparation (plasma separation) and antigen detection with comparable detection ranges as other SPR based sensors. The present disclosure represents an attractive approach for the detection of viruses directly from blood, with comparable assay time (<10 min) and clinically relevant limit of detection (0.1 μg/mL).

Success in containing the spread of viral infections relies on the early and accurate detection of biomarkers in biological fluids, ideally in the infection stages prior to the onset of life-threatening symptoms. In addition, as several viral infections manifest as similar symptoms at the early stages, and most of them can develop into chronic pathologies, any misdiagnosis can lead to severe medical complications leading to death. In this context, the present disclosure demonstrated a biosensing platform with potential portability for deploying to the sites of interest, for example, in remote locations lacking the adequate infrastructure for prompt screening. In some embodiments, multiplexing, and hardware integration this platform can become a practical solution to detect a myriad of other biomarkers, not only the different genera from the Flaviviridae virus family but to other relevant pathologies associated to viral infections, such as the current COVID-19 pandemic caused by the SARS-CoV-2 virus.

A method is performed by an automated system in order to control the plasma separation process. A method is to functionalize and passivate the sensor at the same time with the aim at optimizing sensor preparation time. A method describes how the blood sample is delivered to the microfluidic chip. A method is to prevent polymer swelling to increase the performance of the biosensor in aqueous environments, especially based in cavity-coupling. In this case, aluminum oxide thin film coating is used.

A method involves adding a control measurement, in parallel with the biosensing of the target biomarker. A method, based on the methods previously described, involves the detection of multiple biomarkers from the same sample with the aim at identifying an infection with high confidence. A method involves the integration of this sensor with the optical readout system that allows the implementation of portable biosensing system.

Referring now to FIGS. 1A-1B, 2A, and 5, a method for detecting a biomarker (i.e. a protein caused by an ongoing infection from a virus, a pathogen, a bacterium, or other microorganism, e.g.) within a sample of blood is now described with reference to a flowchart 1000, which begins at Block 1001. For example, the biomarker may comprise at least one of a DENV1-NS1 protein, a DENV2-NS1 protein, or a Dengue virus protein. In some embodiments, the method may further comprise detecting the biomarker in the sample of blood at a concentration less than 0.2 μg/mL.

The method illustratively includes processing the sample of blood with a biosensor 200. (Block 1003). The biosensor 200 illustratively includes a substrate 201, a microfluidic blood plasma separator 202 on the substrate, and a plasmonic array biosensor 203 on the substrate. The microfluidic blood plasma separator 202 illustratively comprises a first inlet 204*a* for receiving the sample of blood, a second inlet 204*b* for receiving a buffer solution, a first outlet 205*a* for outputting the sample of blood, and a second outlet 205*b* for outputting the buffer solution.

As perhaps best seen in FIG. 2A, the plasmonic array biosensor 203 illustratively comprises a dielectric layer 210 (e.g. dielectric epoxy, such as SU-8 photoresist), a membrane layer 211 (e.g. Aluminum oxide) over the dielectric layer, and a conductive layer 212 (e.g. gold) over the membrane layer. The plasmonic array biosensor 203 comprises an ssDNA aptamer layer 213 over the conductive layer to define a sensing surface.

The method illustratively comprises flowing the sample of blood over a sensing surface of the plasmonic array biosensor 203. (Block 1005). The sensing surface of the plasmonic array biosensor 203 has an ssDNA aptamer against the biomarker. The method further includes binding the biomarker in the sample of blood to the ssDNA aptamer of the plasmonic array biosensor 203. (Block 1007). The method further comprises reducing nonselective binding from proteins in the sample of blood based upon a passivation layer on the plasmonic array biosensor 203.

The method also includes flowing a buffer solution and the sample of blood through the microfluidic blood plasma separator 202 until the reflected optical signal stabilizes. The method further includes increasing a flow of the sample of blood until plasma separation occurs to provide a plasma sample from the sample of blood, and performing the detection on the plasma sample. The method comprises incubating the plasma sample from the blood sample, and passing the plasma over the sensing surface of the plasmonic array biosensor 203. The method comprises, subsequently to the passing, flushing the microfluidic blood plasma separator 202 with the buffer solution.

The method also includes detecting the biomarker in the sample of blood based upon a LSPR altering a reflected optical signal from the plasmonic array biosensor 203. (Block 1009). In particular, the detection comprises shining an optical signal into the plasmonic array biosensor 203 and detecting the reflected optical signal. The method ends at Block 1011.

Figure 6:
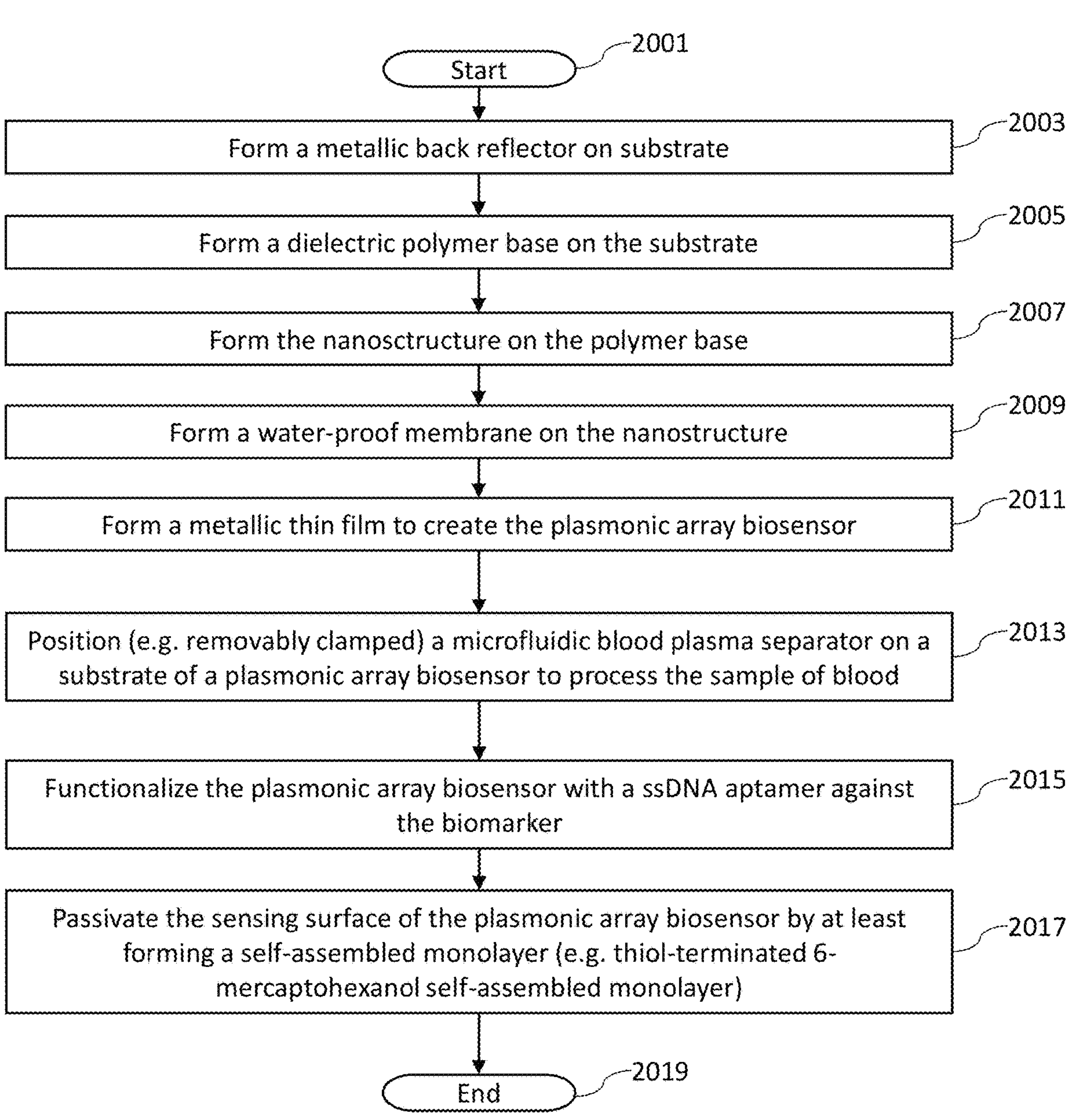
FIG. 6 is a flowchart of a method for making a plasmonic array biosensor for detecting a biomarker, according to the present disclosure.

Referring now to FIGS. 1A-1B and 6, a method for making a plasmonic array biosensor for detecting a biomarker within a sample of blood is now described with reference to a flowchart 2000, which begins at Block 2001.

The method illustratively includes forming a metallic back reflector on a substrate 201. (Block 2003). The method comprises forming a dielectric polymer base 210 on the metallic back reflector. (Block 2005). The method comprises forming a nanostructure on the polymer base 210. (Block 2007). The method comprises forming a water proof membrane 211 on the nanostructure. (Block 2009). For example, the water proof membrane 211 may comprise aluminum oxide. The method comprises forming a metallic thin film 212 to create the plasmonic array biosensor 203. (Block 2011).

The method illustratively includes positioning a microfluidic blood plasma separator 202 on a substrate 201 of a plasmonic array biosensor 203 to process the sample of blood. (Block 2013). In some embodiments, the microfluidic blood plasma separator 202 may be removably clamped onto the substrate 201, and other embodiments, it may be attached via an adhesive layer.

The method illustratively comprises functionalizing the plasmonic array biosensor 203 with an ssDNA aptamer against the biomarker. (Block 2015). A sensing surface of the plasmonic array biosensor 203 is to bind to the biomarker in the sample of blood. The plasmonic array biosensor 203 is to detect the biomarker in the sample of blood based upon a LSPR signal.

The method further comprises passivating the sensing surface of the plasmonic array biosensor 203 by at least forming a self-assembled monolayer. (Block 2017). For example, the self-assembled monolayer may comprise a thiol-terminated 6-mercaptohexanol self-assembled monolayer.

The plasmonic array biosensor 203 comprises a hole-disc array 206. For example, the hole-disc array 206 may have period of 0.5-0.6 μm, a diameter of 0.1-0.3 μm, and a relief depth of 0.2-0.4 μm. The method ends at Block 2019.

In the following, a discussion of an example embodiment of a method for making the plasmonic array biosensor 203. Glass slides (3"×1") are cut into square-shaped (1"×1") slides using a diamond scriber. Each glass slide is thoroughly cleaned with acetone, isopropyl alcohol and deionized water, and then dried with nitrogen gas. A thin layer of titanium (5 nm) followed by gold (100 nm) is deposited onto the clean glass substrate using electron-beam deposition. An epoxy-based negative photoresist SU-8 2000.5 used to create the dielectric cavity, is spin-coated at 3000 rpm for one minute onto the substrate to achieve the desired thickness (~700 nm). The substrate is then pre-baked at 95° C. for a minute. A polydimethylsiloxane (PDMS)-based stamp, containing the inverse nanopatterned array structure, is used to thermally emboss the hole-disk array onto the substrate. The substrate is then exposed under UV light (365 nm) for 5 minutes to crosslink and cure the photoresist. A thin 20 nm conformal coating of aluminum oxide ($Al_2O_3$) is deposited on the embossed substrate via atomic layer deposition. This is to prevent water diffusion into the polymer that may cause swelling. The substrate is finally coated with a thin film of titanium (3 nm) and gold (30 nm) using e-beam evaporation to create the top plasmonic nanopatterned structure.

In the following, a discussion of an example embodiment of a method for making the microfluidic blood plasma separator 202. The microfluidic blood plasma separator 202 may be fabricated using the standard soft lithography technique. In particular, a dark field mask containing the microfluidic channel pattern is printed onto a transparent sheet. SU-8 2050 is spin-coated on a pristine silicon wafer, previously treated with hexamethyldisilazane (HDMS) adhesion promoter, at 3000 rpm for one minute to produce~50 μm thick layer, followed by solvent evaporation at 65° C. for 3 minutes and at 95° C. for 8 minutes. UV-lithography is performed onto the coated wafer, followed by a post-exposure baking at 95° C. for 5 minutes. The wafer is developed in propylene glycol monomethyl ether acetate for 5 minutes followed by isopropyl alcohol and deionized water rinse and dried with nitrogen gas. The wafer is fluorinated with tridecafluoro-1,1,2,2-tetrahydrooctyl triethoxysilane to make the surface hydrophobic. Finally, the microfluidic chip is fabricated using PDMS elastomer mixed with its curing agent in a 10:1% w/w ratio and poured over the fluorinated silicon master mold. Once degassed, the PDMS-silicon mold is baked at 75° C. in a convection oven for 2 hours, demolded, cut, and punctured with the appropriate inlets and outlets. The microfluidic chip is laminated onto the sensor's surface and kept in a place using acrylic clamps. After each assay, the microfluidic chip was thoroughly cleaned in deionized water, isopropyl alcohol and followed by 10 minutes of sonication in acetone.

In the following, a discussion of an example embodiment of the step for functionalizing the plasmonic array biosensor 203 with an ssDNA aptamer against the biomarker. The sensors are cleaned with ethanol and deionized water, and then dried with nitrogen gas prior to functionalization. Hydrophilic, about 1 mm thick, PDMS film with 3 mm hole is placed on top of each sensor to contain 2 μL of aptamer solution. Hydrophilicity of PDMS surface was introduced by surface modification with polyvinyl alcohol (PVA). In brief, the PDMS is activated in an oxygen plasma chamber for 5 min and incubated in 0.1% w/v aqueous solution of PVA. The petri dish containing the samples is sealed with parafilm and placed on a shaker at 200 rpm for 4 hours. Post-incubation period, each sensor is washed with PBS buffer three times to remove any unbound aptamers. Surface passivation: right after surface functionalization, 2 μL of 30 μM methanolic solution of 6-mercaptahexanol is added to each sensor. The petri dish is re-sealed with parafilm and stored at 4° C. at least 12 hours. The sensors are cleaned with PBS buffer three times to remove unreacted MCH. 2 μL of PBS is added to each sensor, thereafter, to keep them hydrated until used.

Many modifications and other embodiments of the present disclosure will come to the mind of one skilled in the art having the benefit of the teachings presented in the foregoing descriptions and the associated drawings. Therefore, it is understood that the present disclosure is not to be limited to the specific embodiments disclosed, and that modifications and embodiments are intended to be included within the scope of the appended claims.

REFERENCES (the contents of which are hereby incorporated by reference in their entirety)

Rodriguez-Roche, R.; Gould, E. A. Understanding the Dengue Viruses and Progress towards Their Control. Biomed Res. Int. 2013, 2013, 1-20. https://doi.org/10.1155/2013/690835.

(2) Guzman, M. G.; Halstead, S. B.; Artsob, H.; Buchy, P.; Farrar, J.; Gubler, D. J.; Hunsperger, E.; Kroeger, A.; Margolis, H. S.; Martí-nez, E.; Nathan, M. B.; Pelegrino, J. L.; Simmons, C.; Yoksan, S.; Peeling, R. W. Dengue: A Continuing Global Threat. Nat. Rev. Microbiol. 2010, 8 (12), S7-S16. https://doi.org/10.1038/nrmicro2460.

(3) Tuiskunen Bäck, A.; Lundkvist, Å. Dengue Viruses—an Overview. Infect. Ecol. Epidemiol. 2013, 3 (1), 19839. https://doi.org/10.3402/iee.v3i0.19839.

(4) Yung, C. F.; Lee, K. S.; Thein, T. L.; Tan, L. K.; Gan, V. C.; Wong, J. G. X.; Lye, D. C.; Ng, L. C.; Leo, Y. S. Dengue Serotype-Specific Differences in Clinical Manifestation, Laboratory Parameters and Risk of Severe Disease in Adults, Singapore. Am. J. Trop. Med. Hyg. 2015, 92 (5), 999-1005. https://doi.org/10.4269/ajtmh.14-0628.

(5) Whitehorn, J.; Simmons, C. P. The Pathogenesis of Dengue. Vaccine 2011, 29 (42), 7221-7228. https://doi.org/10.1016/J.VACCINE.2011.07.022.

(6) Coller, B.-A. G.; Clements, D. E. Dengue Vaccines: Progress and Challenges. Curr. Opin. Immunol. 2011, 23 (3), 391-398. https://doi.org/10.1016/J.COI.2011.03.005.

(7) Chokephaibulkit, K.; Perng, G. C. Challenges for the Formulation of a Universal Vaccine against Dengue. Exp. Biol. Med. 2013, 238 (5), 566-578. https://doi.org/10.1177/1535370212473703.

(8) Rosa, B. R.; Cunha, A. J. L. A. Da; Medronho, R. D. A. Efficacy, Immunogenicity and Safety of a Recombinant Tetravalent Dengue Vaccine (CYD-TDV) in Children Aged 2-17 Years: Systematic Review and Meta-Analysis. BMJ Open 2019, 9 (3), 1-9. https://doi.org/10.1136/bmjopen-2017-019368.

(9) World Health Organization. Global Vaccine Safety. GACVS Statement on Dengvaxia® (CYD-TDV). World Health Organization, 2017. Available at: https://www.who.int/vaccine_safety/committee/GACVS-StatementonDengvaxia-CYD-TDV/en/.

(10) Vazquez, S.; Lemos, G.; Pupo, M.; Ganzón, O.; Palenzuela, D.; Indart, A.; Guzman, M. G. Diagnosis of Dengue Virus Infection by the Visual and Simple AuBioDOT Immunoglobulin M Capture System. Clin. Diagn. Lab. Immunol. 2003, 10 (6), 1074-1077. https://doi.org/10.1128/CDLI.10.6.1074-1077.2003.

(11) Alcon, S.; Talarmin, A.; Debruyne, M.; Falconar, A.; Deubel, V.; Flamand, M. Enzyme-Linked Immunosorbent Assay Specific to Dengue Virus Type 1 Nonstructural Protein NS1 Reveals Circulation of the Antigen in the Blood during the Acute Phase of Disease in Patients Experiencing Primary or Secondary Infections. J. Clin. Microbiol. 2002, 40 (2), 376-381. https://doi.org/10.1128/JCM.40.02.376-381.2002.

(12) Sa-Ngasang, A.; Wibulwattanakij, S.; Chanama, S.; O-Rapinpatipat, A.; A-Nuegoonpipat, A.; Anantapreecha, S.; Sawanpanyalert, P.; Kurane, I. Evaluation of RT-PCR as a Tool for Diagnosis of Secondary Dengue Virus Infection. Jpn. J. Infect. Dis. 2003, 56 (5-6), 205-209.

(13) Lolekha, R.; Chokephaibulkit, K.; Yoksan, S.; Vanprapar, N.; Phongsamart, W.; Chearskul, S. Diagnosis of Dengue Infection Using Various Diagnostic Tests in the Early Stage of Illness. Southeast Asian J. Trop. Med. Public Health 2004, 35 (2), 391-395.

(14) Sharma, S.; Kumari, R.; Varshney, S. K.; Lahiri, B. Optical Biosensing with Electromagnetic Nanostructures. Rev. Phys. 2020, 5. https://doi.org/10.1016/j.revip.2020.100044.

(15) Yang, T.; Chen, S.; He, X.; Guo, H.; Sun, X. How to Convincingly Measure Low Concentration Samples with Optical Label-Free Biosensors. Sens Actuators B Chem. 2020, 306, 127568. https://doi.org/10.1016/j.snb.2019.127568.

(16) Chanda, D.; Shigeta, K.; Truong, T.; Lui, E.; Mihi, A.; Schulmerich, M.; Braun, P. V.; Bhargava, R.; Rogers, J. A. Coupling of Plasmonic and Optical Cavity Modes in Quasi-Three-Dimensional Plasmonic Crystals. Nat. Commun. 2011, 2 (1), 479. https://doi.org/10.1038/ncomms1487.

(17) Vázquez-Guardado, A.; Smith, A.; Wilson, W.; Ortega, J.; Perez, J. M.; Chanda, D. Hybrid Cavity-Coupled Plasmonic Biosensors for Low Concentration, Label-Free and Selective Biomolecular Detection. Opt. Express 2016, 24 (22). https://doi.org/10.1364/OE.24.025785.

(18) Vázquez-Guardado, A.; Barkam, S.; Peppler, M.; Biswas, A.; Dennis, W.; Das, S.; Seal, S.; Chanda, D. Enzyme-Free Plasmonic Biosensor for Direct Detection of Neurotransmitter Dopamine from Whole Blood. Nano Lett. 2019, 19 (1). https://doi.org/10.1021/acs.nanolett.8b04253.

(19) Vázquez-Guardado, A.; Safaei, A.; Modak, S.; Franklin, D.; Chanda, D. Hybrid Coupling Mechanism in a System Supporting High Order Diffraction, Plasmonic, and Cavity Resonances. Phys. Rev. Lett. 2014, 113 (26). https://doi.org/10.1103/PhysRevLett.113.263902.

(20) Toh, S. Y.; Citartan, M.; Gopinath, S. C. B.; Tang, T. H. Aptamers as a Replacement for Antibodies in Enzyme-Linked Immunosorbent Assay. Biosens. Bioelectron. 2015, 64, 392-403. https://doi.org/10.1016/j.bios.2014.09.026.

(21) Herne, T. M.; Tarlov, M. J. Characterization of DNA Probes Immobilized on Gold Surfaces. J. Am. Chem. Soc. 1997, 119 (38), 8916-8920. https://doi.org/10.1021/ja9719586.

(22) Chiu, T. C.; Huang, C. C. Aptamer-Functionalized Nano-Biosensors; 2009; Vol. 9. https://doi.org/10.3390/s91210356.

(23) Tuerk, C.; Gold, L. Systematic Evolution of Ligands by Exponential Enrichment: RNA Ligands to Bacteriophage T4 DNA Polymerase. Science 1990, 249 (4968), 505-510. https://doi.org/10.1126/science.2200121.

(24) Ellington, A. D.; Szostak, J. W. In Vitro Selection of RNA Molecules That Bind Specific Ligands. Nature 1990, 346 (6287), 818-822. https://doi.org/10.1038/346818a0.

(25) Liu, J.; Wagan, S.; Davila Morris, M.; Taylor, J.; White, R. J. Achieving Reproducible Performance of Electrochemical, Folding Aptamer-Based Sensors on Microelectrodes: Challenges and Prospects. Anal. Chem. 2014, 86 (22), 11417-11424. https://doi.org/10.1021/ac503407e.

(26) Cash, K. J.; Heeger, A. J.; Plaxco, K. W.; Xiao, Y. Optimization of a Reusable, DNA Pseudoknot-Based Electrochemical Sensor for Sequence-Specific DNA Detection in Blood Serum. Anal. Chem. 2009, 81 (2), 656-661. https://doi.org/10.1021/ac802011d.

(27) Libraty, D. H.; Young, P. R.; Pickering, D.; Endy, T. P.; Kalayanarooj, S.; Green, S.; Vaughn, D. W.; Nisalak, A.; Ennis, F. A.; Rothman, A. L. High Circulating Levels of the Dengue Virus Nonstructural Protein NS1 Early in Dengue Illness Correlate with the Development of Dengue Hemorrhagic Fever. J. Infect. Dis. 2002, 186 (8), 1165-1168. https://doi.org/10.1086/343813.

(28) Ameling, R.; Langguth, L.; Hentschel, M.; Mesch, M.; Braun, P. V.; Giessen, H. Cavity-Enhanced Localized Plasmon Resonance Sensing. Appl. Phys. Lett. 2010, 97 (25), 253116. https://doi.org/10.1063/1.3530795.

(29) Wouters, K.; Puers, R. Diffusing and Swelling in SU-8: Insight in Material Properties and Processing. J. Micromechanics Microengineering 2010, 20 (9), 095013. https://doi.org/10.1088/0960-1317/20/9/095013.

(30) Young, L. B.; Melian, E. B.; Setoh, Y. X.; Young, P. R.; Khromykh, A. A. Last 20 Aa of the West Nile Virus NS1' Protein Are Responsible for Its Retention in Cells and the Formation of Unique Heat-Stable Dimers. J. Gen. Virol. 2015, 96 (5), 1042-1054. https://doi.org/10.1099/vir.0.000053.

(31) Bailey, M. J.; Duehr, J.; Dulin, H.; Broecker, F.; Brown, J. A.; Arumemi, F. O.; Bermudez González, M. C.; Leyva-Grado, V. H.; Evans, M. J.; Simon, V.; Lim, J. K.; Krammer, F.; Hai, R.; Palese, P.; Tan, G. S. Human Antibodies Targeting Zika Virus NS1 Provide Protection against Disease in a Mouse Model. Nat. Commun. 2018, 9 (1), 1-11. https://doi.org/10.1038/s41467-018-07008-0.

(32) Rastogi, M.; Sharma, N.; Singh, S. K. Flavivirus NS1: A Multifaceted Enigmatic Viral Protein. Virol. J. 2016, 13 (1), 1-10. https://doi.org/10.1186/s12985-016-0590-7.

(33) Madeira, F.; Park, Y. mi; Lee, J.; Buso, N.; Gur, T.; Madhusoodanan, N.; Basutkar, P.; Tivey, A. R. N.; Potter, S. C.; Finn, R. D.; Lopez, R. The EMBL-EBI Search and Sequence Analysis Tools APIs in 2019. Nucleic Acids Res. 2019, 47 (W1), W636-W641. https://doi.org/10.1093/nar/gkz268.

(34) Gutsche, I.; Coulibaly, F.; Voss, J. E.; Salmon, J.; D'Alayer, J.; Ermonval, M.; Larquet, E.; Charneau, P.; Krey, T.; Megret, F.; Guittet, E.; Rey, F. A.; Flamand, M. Secreted Dengue Virus Nonstructural Protein NS1 Is an Atypical Barrel-Shaped High-Density Lipoprotein. Proc. Natl. Acad. Sci. 2011, 108 (19), 8003-8008. https://doi.org/10.1073/pnas.1017338108.

(35) Flamand, M.; Megret, F.; Mathieu, M.; Lepault, J.; Rey, F. A.; Deubel, V. Dengue Virus Type 1 Nonstructural Glycoprotein NS1 Is Secreted from Mammalian Cells as a Soluble Hexamer in a Glycosylation-Dependent Fashion. J. Virol. 1999, 73 (7), 6104-6110. https://doi.org/10.1128/jvi.73.7.6104-6110.1999.

(36) Arroyo-Currás, N.; Somerson, J.; Vieira, P. A.; Ploense, K. L.; Kippin, T. E.; Plaxco, K. W. Real-Time Measurement of Small Molecules Directly in Awake, Ambulatory Animals. Proc. Natl. Acad. Sci. 2017, 114 (4), 645-650. https://doi.org/10.1073/pnas.1613458114.

(37) Dykstra, P. H.; Roy, V.; Byrd, C.; Bentley, W. E.; Ghodssi, R. Microfluidic Electrochemical Sensor Array for Characterizing Protein Interactions with Various Functionalized Surfaces. Anal. Chem. 2011, 83 (15), 5920-5927. https://doi.org/10.1021/ac200835s.

(38) Yang, S.; Ündar, A.; Zahn, J. D. A Microfluidic Device for Continuous, Real Time Blood Plasma Separation. Lab Chip 2006, 6 (7), 871-880. https://doi.org/10.1039/B516401J.

(39) Tripathi, S.; Kumar, Y. V. B.; Agrawal, A.; Prabhakar, A.; Joshi, S. S. Microdevice for Plasma Separation from Whole Human Blood Using Bio-Physical and Geometrical Effects. Sci. Rep. 2016, 6 (1), 26749. https://doi.org/10.1038/srep26749.

(40) Martel, J. M.; Toner, M. Particle Focusing in Curved Microfluidic Channels. Sci. Rep. 2013, 3 (1), 3340. https://doi.org/10.1038/srep03340.

(41) Di Carlo, D.; Edd, J. F.; Irimia, D.; Tompkins, R. G.; Toner, M. Equilibrium Separation and Filtration of Particles Using Differential Inertial Focusing. Anal. Chem. 2008, 80 (6), 2204-2211. https://doi.org/10.1021/ac702283m.

(42) Omar, N. A. S.; Fen, Y. W.; Abdullah, J.; Mustapha Kamil, Y.; Daniyal, W. M. E. M. M.; Sadrolhosseini, A. R.; Mandi, M. A. Sensitive Detection of Dengue Virus Type 2 E-Proteins Signals Using Self-Assembled Monolayers/Reduced Graphene Oxide-PAMAM Dendrimer Thin Film-SPR Optical Sensor. Sci. Rep. 2020, 10 (1), 2374. https://doi.org/10.1038/s41598-020-59388-3.

(43) Jahanshahi, P.; Zalnezhad, E.; Sekaran, S. D.; Adikan, F. R. M. Rapid Immunoglobulin M-Based Dengue Diagnostic Test Using Surface Plasmon Resonance Biosensor. Sci. Rep. 2015, 4 (1), 3851. https://doi.org/10.1038/srep03851.

(44) Wong, W. R.; Sekaran, S. D.; Mahamd Adikan, F. R.; Berini, P. Detection of Dengue NS1 Antigen Using Long-Range Surface Plasmon Waveguides. Biosens. Bioelectron. 2016, 78, 132-139. https://doi.org/10.1016/j.bios.2015.11.030.

(45) Chowdhury, A. D.; Takemura, K.; Khorish, I. M.; Nasrin, F.; Ngwe Tun, M. M.; Morita, K.; Park, E. Y. The Detection and Identification of Dengue Virus Serotypes with Quantum Dot and AuNP Regulated Localized Surface Plasmon Resonance. Nanoscale Adv. 2020, 2 (2), 699-709. https://doi.org/10.1039/C9NA00763F.

The invention claimed is:

1. A method for making a plasmonic array biosensor for detecting a biomarker within a sample of blood, the method comprising:

positioning a microfluidic blood plasma separator on a substrate of a plasmonic array biosensor to process the sample of blood; and functionalizing the plasmonic array biosensor with a single stranded DNA (ssDNA) aptamer against the biomarker, a sensing surface of the plasmonic array biosensor to bind to the biomarker in the sample of blood, the plasmonic array biosensor to detect the biomarker in the sample of blood based upon a localized surface plasmon resonance (LSPR) signal, the functionalizing comprising cleaning the plasmonic array biosensor, and forming a hydrophilic film on the cleaned plasmonic array biosensor, the hydrophilic film comprising the ssDNA aptamer, polydimethylsiloxane, and polyvinyl alcohol;

the biomarker comprising at least one of a DENV1-NS1 protein, a DENV2-NS1 protein, or a Dengue virus protein.

2. The method of claim 1 further comprising passivating the sensing surface of the plasmonic array biosensor by at least forming a self-assembled monolayer.

3. The method of claim 2 wherein the self-assembled monolayer comprises a thiol-terminated 6-mercaptohexanol self-assembled monolayer.

4. The method of claim 1 wherein the microfluidic blood plasma separator is removably clamped onto the substrate.

5. The method of claim 1 wherein the plasmonic array biosensor comprising a hole-disc array.

6. The method of claim 5 wherein the hole-disc array has period of 0.5-0.6 μm, a diameter of 0.1-0.3 μm, and a relief depth of 0.2-0.4 μm.

7. The method of claim 1 further comprising forming a metallic back reflector on the plasmonic array biosensor.

8. The method of claim 1 further comprising forming a dielectric polymer base for the plasmonic array biosensor.

9. The method of claim 8 further comprising forming a water proof membrane on the dielectric polymer base.

10. The method of claim 9 wherein the water proof membrane comprises aluminum oxide.

11. A method for making a plasmonic array biosensor for detecting a biomarker within a sample of blood, the method comprising:

positioning a microfluidic blood plasma separator on a substrate of a plasmonic array biosensor to process the sample of blood, the microfluidic blood plasma separator being removably clamped onto the substrate;

functionalizing the plasmonic array biosensor with a single stranded DNA (SSDNA) aptamer against the biomarker, a sensing surface of the plasmonic array biosensor to bind to the biomarker in the sample of blood, the plasmonic array biosensor to detect the biomarker in the sample of blood based upon a localized surface plasmon resonance (LSPR) signal, the functionalizing comprising cleaning the plasmonic array biosensor, and forming a hydrophilic film on the cleaned plasmonic array biosensor, the hydrophilic film comprising the ssDNA aptamer, polydimethylsiloxane, and polyvinyl alcohol; and passivating the sensing surface of the plasmonic array biosensor by at least forming a self-assembled monolayer;

the biomarker comprising at least one of a DENV1-NS1 protein, a DENV2-NS1 protein, or a Dengue virus protein.

12. The method of claim 11 wherein the self-assembled monolayer comprises a thiol-terminated 6-mercaptohexanol self-assembled monolayer.

13. The method of claim 11 wherein the plasmonic array biosensor comprising a hole-disc array.

14. The method of claim 13 wherein the hole-disc array has period of 0.5-0.6 μm, a diameter of 0.1-0.3 μm, and a relief depth of 0.2-0.4 μm.

15. The method of claim 11 further comprising forming a metallic back reflector on the plasmonic array biosensor.

16. The method of claim 11 further comprising forming a dielectric polymer base for the plasmonic array biosensor.

17. The method of claim 16 further comprising forming a water proof membrane on the dielectric polymer base.

18. The method of claim 17 wherein the water proof membrane comprises aluminum oxide.

19. A method for making a plasmonic array biosensor for detecting a biomarker within a sample of blood, the method comprising:

positioning a microfluidic blood plasma separator on a substrate of a plasmonic array biosensor to process the sample of blood, the plasmonic array biosensor comprising a hole-disc array comprising gold, the microfluidic blood plasma separator being removably clamped onto the substrate;

functionalizing the plasmonic array biosensor with a single stranded DNA (ssDNA) aptamer against the biomarker, a sensing surface of the plasmonic array biosensor to bind to the biomarker in the sample of blood, the plasmonic array biosensor to detect the biomarker in the sample of blood based upon a localized surface plasmon resonance (LSPR) signal, the functionalizing comprising cleaning the plasmonic array biosensor, and forming a hydrophilic film on the cleaned plasmonic array biosensor, the hydrophilic film comprising the ssDNA aptamer, polydimethylsiloxane, and polyvinyl alcohol; and passivating the sensing surface of the plasmonic array biosensor by at least forming a self-assembled monolayer, the self-assembled monolayer comprising a thiol-terminated 6-mercaptohexanol self-assembled monolayer;

the biomarker comprising at least one of a DENV1-NS1 protein, a DENV2-NS1 protein, or a Dengue virus protein.

20. The method of claim 19 wherein the thiol-terminated 6-mercaptohexanol self-assembled monolayer binds covalently to the gold.

* * * * *